(12) United States Patent
Edmondson et al.

(10) Patent No.: US 7,098,239 B2
(45) Date of Patent: Aug. 29, 2006

(54) DIPEPTIDYL PEPTIDASE INHIBITORS FOR THE TREATMENT OF DIABETES

(75) Inventors: Scott D. Edmondson, New York, NY (US); Emma Parmee, Scotch Plains, NJ (US); Ann E. Weber, Scotch Plains, NJ (US); Jinyou Xu, Scotch Plains, NJ (US)

(73) Assignee: Merck & Co., Inc, Rahway, NJ (US)

( * ) Notice: Subject to any disclaimer, the term of this patent is extended or adjusted under 35 U.S.C. 154(b) by 419 days.

(21) Appl. No.: 10/481,319

(22) PCT Filed: Jun. 19, 2002

(86) PCT No.: PCT/US02/19432

§ 371 (c)(1),
(2), (4) Date: Dec. 18, 2003

(87) PCT Pub. No.: WO03/000180

PCT Pub. Date: Jan. 3, 2003

(65) Prior Publication Data

US 2004/0176428 A1    Sep. 9, 2004

Related U.S. Application Data

(60) Provisional application No. 60/299,464, filed on Jun. 20, 2001.

(51) Int. Cl.
*A61K 31/40* (2006.01)
*C07D 207/00* (2006.01)

(52) U.S. Cl. ..................................... 514/423; 548/537

(58) Field of Classification Search ................ 514/423; 548/537
See application file for complete search history.

(56) References Cited

U.S. PATENT DOCUMENTS

| | | | |
|---|---|---|---|
| 4,386,090 A | 5/1983 | Moinet et al. | |
| 5,939,560 A | 8/1999 | Jenkins et al. | |
| 6,903,130 B1 * | 6/2005 | Lamberty et al. | 514/423 |
| 6,911,467 B1 * | 6/2005 | Evans | 514/423 |
| 6,946,468 B1 * | 9/2005 | Boyle et al. | 514/254.01 |
| 7,026,316 B1 * | 4/2006 | Ashton et al. | 514/242 |

FOREIGN PATENT DOCUMENTS

| | | |
|---|---|---|
| WO | WO 97/40832 A1 | 11/1997 |
| WO | WO 98/19998 A2 | 5/1998 |
| WO | WO 98/19998 A3 | 5/1998 |
| WO | WO 00/34241 A1 | 6/2000 |
| WO | WO 01/34594 A1 | 5/2001 |
| WO | WO 01/96295 A2 | 12/2001 |
| WO | WO 01/96295 A3 | 12/2001 |
| WO | WO 02/02560 A2 | 1/2002 |
| WO | WO 02/02560 A3 | 1/2002 |
| WO | WO 02/076450 A1 | 10/2002 |
| WO | WO 03/000180 A2 | 1/2003 |
| WO | WO 03/000180 A3 | 1/2003 |
| WO | WO 03/000181 A2 | 1/2003 |
| WO | WO 03/000181 A3 | 1/2003 |
| WO | WO 03/004498 A1 | 1/2003 |
| WO | WO 03/082817 A2 | 10/2003 |

OTHER PUBLICATIONS

Expert Opinion onTherapeutic Patents, "Novel N-substituted-2-cyanopyrrolidines as potent inhibitors of dipeptidyl peptidase IV in the treatment of non-insulin-dependent diabetes mellitus", vol. 10 (#12) p. 1937-1942 (2000).
Expert Opinion on Investig. Drugs, "Gut peptides in the treatment of diabetes mellitus", (2004) 13 (3) 177-188.
Expert Opinion on Investig. Drugs, "Therapeutic potential of dipeptidyl peptidase IV inhibitors for the treatment of type 2 diabetes", (2003) 12: 87-100.
Expert Opinion on Therapeutic Patents, "Dipeptidyl peptidase IV inhibitors as new therapeutic agents for the treatment of Type 2 diabetes", (2003) 13: 499-510.

* cited by examiner

*Primary Examiner*—Deborah C. Lambkin
(74) *Attorney, Agent, or Firm*—Philippe L. Durette; Melvin Winokur

(57) ABSTRACT

Compounds having Formula I, including pharmaceutically acceptable salts and prodrugs thereof: (Formula I) are inhibitors of the dipep tidyl peptidase-IV enzyme (DP-IV), and are useful in the treatment of DP-IV mediated diseases and conditions, such as non-insulin dependent diabetes mellitus.

19 Claims, No Drawings

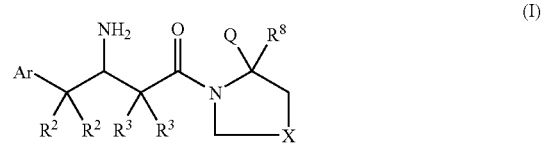

DIPEPTIDYL PEPTIDASE INHIBITORS FOR THE TREATMENT OF DIABETES

CROSS REFERENCE TO RELATED APPLICATIONS

This application is the National Stage of International Application No. PCT/US02/19432 filed 19 Jun. 2002, which claims the benefit under 35 U.S.C. 119(e) of U.S. Provisional Application No. 60/299,464, filed 20 Jun. 2001.

FIELD OF THE INVENTION

The instant invention is concerned with a novel class of dipeptidyl peptidase inhibitors, including pharmaceutically acceptable salts and prodrugs thereof, which are useful as therapeutic compounds, particularly in the treatment of Type 2 diabetes mellitus, often referred to as non-insulin dependent diabetes (NIDDM), and of conditions that are often associated with this disease, such as obesity and lipid disorders.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV enzyme are also under investigation as drugs that may be useful in the treatment of diabetes, and particularly type 2 diabetes. See for example WO 97/40832 and WO 98/19998. The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors may also have other therapeutic utilities, as discussed elsewhere in this application. DP-IV inhibitors have not been studied extensively to date, especially for utilities other than diabetes. New compounds are needed so that improved DP-IV inhibitors can be found for the treatment of diabetes and potentially other diseases and conditions.

SUMMARY OF THE INVENTION

A new class of DP-IV inhibitors is described herein. They may be effective in the treatment of Type 2 diabetes and other DP-IV modulated diseases. The class of compounds is defined by formula I below, including pharmaceutically acceptable salts and prodrugs.

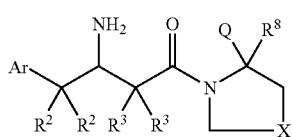

I

In Formula I, X is selected from the group consisting of: $CR^{10}R^{11}$, S, SO, $SO_2$, and $CR^{10}R^9$, with the proviso that when X is $CR^{10}R^9$, Q and $R^8$ are both H;

Ar is selected from the group consisting of:
(1) phenyl,
(2) naphthyl,
(3) thienyl, and
(4) benzothiophenyl;

wherein Ar is optionally substituted with 1–5 groups $R^1$;
$R^1$ is selected from the group consisting of:
(1) halogen,
(2) $C_{1-6}$alkyl, which is linear or branched and is optionally substituted with 1–5 halogens,
(3) $OC_{1-6}$alkyl, which is linear or branched and is optionally substituted with 1–5 halogens, and
(4) CN;

Each $R^2$ is independently selected from the group consisting of H, OH, halogen and $C_{1-6}$alkyl, wherein $C_{1-6}$alkyl is linear or branched and is optionally substituted with 1–5 halogens, wherein the two groups $R^2$ can optionally be joined to form a $C_{3-6}$cycloalkyl, which is optionally substituted with 1–3 halogens;

Each $R^3$ is independently selected from the group consisting of H, halogen and $C_{1-6}$alkyl, wherein $C_{1-6}$alkyl is linear or branched and is optionally substituted with 1–5 halogens, wherein the two groups $R^3$ can optionally be joined to form a $C_{3-6}$cycloalkyl, which is optionally substituted with 1–3 halogens;

Q is selected from the group consisting of:
(1) H,
(2) C(=O)$NR^4Z$, and
(3) CN;

$R^4$ is selected from the group consisting of
(1) H, and
(2) $C_{1-6}$alkyl, which is linear or branched and is optionally substituted with 1–5 halogens;

Z is selected from the group consisting of:
(1) phenyl, which is optionally substituted with 1–5 substituents independently selected from halogen and $R^6$,
(2) $C_{1-6}$alkyl, which is linear or branched and is optionally substituted with 1–7 substituents independently selected from (a) 0–5 halogens, and (b) 0–2 substituents selected from the group consisting of (a) hydroxy,
(b) $CO_2H$,
(c) $CO_2C_{1-6}$alkyl,
(d) phenyl,
(e) naphthyl,
(f) $C_{3-6}$ cycloalkyl,
(g) a 5- or 6-membered heterocycle which may be saturated or unsaturated comprising 1–4 heteroatoms independently selected from N, S and O; and
(h) an 8–10 membered bicyclic ring system which may be saturated or unsaturated comprising (a) two fused heterocyclic rings, each heterocyclic ring having 1–4 heteroatoms selected from N, S and O, or (b) a benzene ring fused to a 5- or 6-membered heterocycle having 1–3 heteroatoms; wherein said $C_{3-6}$cycloalkyl, phenyl and naphthyl are optionally substituted with 1–5 substituents independently selected from halogen and $R^6$, and said 5 or 6-membered heterocycle and said 8–10 membered bicyclic ring system are each optionally substituted with 1–5 substituents independently selected from oxo, OH, halogen, and $R^6$; and (3) $C_{3-6}$cycloalkyl, which is optionally substituted with 1–3 groups independently selected from halogen, hydroxy, $CO_2H$, $CO_2C_{1-6}$alkyl, $C_{1-6}$alkyl, and $OC_{1-6}$alkyl, said $CO_2C_{1-6}$alkyl, $C_{1-6}$alkyl, and $OC_{1-6}$alkyl being linear or branched and optionally substituted with 1–5 halogens;

$R^6$ is selected from the group consisting of:
(1) OH,
(2) CN,
(3) $C_{3-6}$ cycloalkyl optionally substituted with 1–3 groups independently selected from hydroxy, halogen, $CO_2H$, $CO_2C_{1-6}$alkyl, $C_{1-6}$ alkyl, and $OC_{1-6}$alkyl, wherein said $C_{1-6}$alkyl, $OC_{1-6}$alkyl and $CO_2C_{1-6}$alkyl are linear or branched and are optionally substituted with 1–6 substituents independently selected from 0–5 halogens and 0–1 substituents selected from $CO_2C_{1-6}$alkyl, $CO_2H$ and $OC_{1-6}$alkyl, said $CO_2C_{1-6}$alkyl and $OC_{1-6}$alkyl substituents being linear or branched and optionally substituted with 1–5 halogens,
(4) $C_{1-10}$alkyl, which is linear or branched and is optionally substituted with 1–7 substituents independently selected from 0–5 halogen atoms and 0–2 groups independently selected from
(a) OH,
(b) $CO_2H$,
(c) $CO_2C_{1-6}$alkyl, which may be linear or branched and is optionally substituted with 1–5 halogens,
(d) a 5- or 6-membered heterocycle which may be saturated or unsaturated comprising 1–4 heteroatoms independently selected from N, S and O, optionally substituted with 1–3 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
(e) an 8–10 membered bicyclic ring system which may be saturated or unsaturated comprising (i) two fused heterocyclic rings, each heterocyclic ring having 1–4 heteroatoms independently selected from N, S and O, or (ii) a 5- or 6-membered heterocycle having 1–3 heteroatoms independently selected from N, S and O fused to a benzene ring, wherein said bicyclic ring system is optionally substituted with 1–5 substituents independently selected from oxo, OH, halogen, $C_{1-6}$alkyl, and $OC_{1-6}$alkyl, said $C_{1-6}$alkyl and $OC_{1-}$ 6alkyl being linear or branched and optionally substituted with 1–5 halogens;
(f) $CONR^7R^7$,
(g) $SO_2NR^7R^7$,
(h) $NR^7C(O)R^7$,
(i) $NR^7C(O)NR^7R^7$,
(j) $N^7CO_2R^5$,
(k) $OC(O)R^7$,
(l) $OC(O)NR^7R^7$,
(m) $NR^7S(O)_2R^5$,
(n) $NR^7R^7$,
(o) phenyl, which is optionally substituted with 1–5 groups independently selected from halogen, OH, $C_{1-6}$alkyl, $OC_{1-6}$alkyl, $CO_2H$, and $CO_2C_{1-6}$alkyl, said $C_{1-6}$alkyl, $OC_{1-6}$alkyl, and $CO_2C_{1-6}$alkyl being linear or branched and optionally substituted with 1–6 substituents independently selected from 0–1 C3–6 cycloalkyl and 0–5 halogens, and
(p) $C_{3-6}$cycloalkyl, which is optionally substituted with 1–6 halogens;
(5) $OC_{1-10}$alkyl, which is linear or branched and is optionally substituted with 1–7 groups independently selected from 0–5 halogen atoms and 0–2 substituents selected from
(a) OH,
(b) $CO_2H$,
(c) $CO_2C_{1-6}$alkyl, which may be linear or branched and is optionally substituted with 1–5 halogens,
(d) a 5- or 6-membered heterocycle which may be saturated or unsaturated comprising 1–4 heteroatoms independently selected from N, S and O, optionally substituted with 1–3 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
(e) an 8–10 membered bicyclic ring system which may be saturated or unsaturated comprising (i) two fused heterocyclic rings, each heterocyclic ring having 1–4 heteroatoms independently selected from N, S and O, or (ii) a 5- or 6-membered heterocycle having 1–3 heteroatoms independently selected from N, S and O fused to a benzene ring, wherein said bicyclic ring system is optionally substituted with 1–5 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
(f) $CONR^7R^7$,
(g) $SO_2NR^7R^7$,
(h) $NR^7C(O)R^7$,
(i) $NR^7C(O)NR^7R^7$,
(j) $NR^7CO_2R^5$,
(k) $OC(O)R^7$,
(l) $OC(O)NR^7R^7$,
(m) $NR^7S(O)_2R^5$,
(n) $NR^7R^7$,
(o) phenyl, which is optionally substituted with 1–5 groups independently selected from halogen, OH, $C_{1-6}$alkyl, $OC_{1-6}$alkyl, $CO_2H$, and $CO_2C_{1-6}$alkyl, said $C_{1-6}$alkyl, $OC_{1-6}$alkyl, and $CO_2C_{1-6}$alkyl being linear or branched and optionally substituted with 1–6 substituents independently selected from 0–1 C3–6cycloalkyl and 0–5 halogens, and
(p) $C_{3-6}$cycloalkyl, which is optionally substituted with 1–6 halogens;
(6) $CO_2H$;
(7) $CO_2C_{1-6}$ alkyl, which may be linear or branched and is optionally substituted with 1–5 halogens;
(8) a 5- or 6-membered heterocycle which may be saturated or unsaturated comprising 1–4 heteroatoms independently selected from N, S and O, said heterocycle being optionally substituted with 1–3 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
(9) an 8–10 membered bicyclic ring system which may be saturated or unsaturated comprising (a) two fused heterocyclic rings, each heterocyclic ring having 1–4 heteroatoms independently selected from N, S and O, or (b) a 5- or 6-membered heterocycle having 1–3 heteroatoms independently selected from N, S and O fused to a benzene ring, said bicyclic ring system being optionally substituted with 1–5 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
(10) $CONR^7R^7$;
(11) $SO_2NR^7R^7$;
(12) $NR^7C(O)R^7$;
(13) $NR^7C(O)NR^7R^7$;
(14) $NR^7CO_2R^5$;
(15) $OC(O)R^7$;
(16) $OC(O)NR^7R^7$;
(17) $NR^7S(O)_2R^5$;
(18) $NR^7R^7$; and
(19) phenyl, which is optionally substituted with 1–5 groups independently selected from halogen, OH, $C_{1-6}$alkyl, $OC_{1-6}$alkyl, $CO_2H$, and $CO_2C_{1-6}$alkyl, said $C_{1-6}$alkyl, $OC_{1-6}$alkyl, and $CO_2C_{1-6}$alkyl being linear or branched and optionally substituted with 1–5 halogens;
$R^5$ is selected from the group consisting of phenyl, $C_{3-6}$cycloalkyl and $C_{1-6}$alkyl, wherein $C_{1-6}$alkyl is linear or branched and is optionally substituted with 1–6 substituents independently selected from 0–5 halogens and 0–1 phenyl, wherein said optional phenyl substituent and said $R^5$ when R5 is phenyl or $C_{3-6}$cycloalkyl are optionally substituted with 1–5 substituents independently selected from halogen, OH, $C_{1-5}$alkyl, and $OC_{1-5}$alkyl, said $C_{1-5}$alkyl and $OC_{1-5}$alkyl being linear or branched and optionally substituted with 1–5 halogens;
$R^7$ is selected from
(1) H, and
(2) $R^5$;
$R^8$ is selected from
(1) H, and
(2) $C_{1-6}$allyl, which is linear or branched and is optionally substituted with 1–5 halogens;
$R^9$ is $C(=O)NR^4Z$; and
$R^{10}$ and $R^{11}$ are each selected from the group consisting of H, F and $C_{1-6}$ alkyl, which is linear or branched and is optionally substituted with 1–5 halogens.

DETAILED DESCRIPTION OF THE INVENTION

The compounds having Formula I have numerous preferred embodiments, which are described below.

In embodiments of Formula I, $R_2$ is H. In other embodiments, $R_3$ is H. In still other embodiments, $R^2$ and $R^3$ are both H.

In other embodiments, Ar is phenyl, which is optionally substituted as described above.

In other embodiments, $R^4$ is H.

Other embodiments comprise compounds having Formula I in which Q is C(=O)NHZ, Z is selected from $CH_2$phenyl, cyclohexyl and cyclopentyl, and $R^9$ is C(=O)NHCH$_2$phenyl, where phenyl, cyclohexyl and cyclopentyl are optionally substituted as described above.

The group X in preferred embodiments is selected from the group consisting of: $CH_2$, CHF, $CF_2$, S, SO, $SO_2$, and $CHR^9$, with the proviso that when X is $CHR^9$, Q and $R^8$ are both H.

In other groups of compounds, $R^8$ is H.

In the compounds described above, the 8–10 membered bicyclic ring system is preferably selected from the group consisting of indole, indoline, benzofuran, benzothiophene, benzoxazole, benzisoxazole, benzothiazole, benzisothiazole, benzimidazole, benzimidazoline, quinoline, quinazoline, dihydroquinazoline, dihydroquinoline, isoquinoline, tetrahydroisoquinoline, and dihydroisoquinoline, substituted as described above. Indole is a preferred 8–10 membered bicyclic ring system.

Preferably 5- or 6-membered heterocycles are selected from furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, and tetrazolidine. More preferred heterocycles include imidazole, morpholine, pyrazole, pyridine, tetrazole, thiazole and triazole.

Definitions

"Ac" is acetyl, which is $CH_3C(O)$—.

"Alkyl", as well as other groups having the prefix "alk", such as alkoxy or alkanoyl, means carbon chains which may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a mono- or bicyclic saturated carbocyclic ring having from 3 to 10 carbon atoms. The term also can refer to a cycloalkyl ring fused to another ring such as an aromatic ring. Examples of cycloalkyl include cyclopropyl, cyclopentyl, cyclohexyl, cycloheptyl, and the like.

"Aryl" (and "arylene") means a mono- or polycyclic aromatic ring system containing only carbon ring atoms. The term "aryl" also includes an aryl group fused to a cycloalkyl or heterocycle, where aryl refers to the aromatic portion. The preferred aryls are phenyl and naphthyl. The most preferred aryl is phenyl.

"Heterocycle" means a saturated or unsaturated ring (including aromatic rings) containing at least one heteroatom selected from N, S and O (including SO and $SO_2$). Examples of heterocycles include tetrahydrofuran, piperazine, morpholine and sulfolane.

"Heteroaryl" (and heteroarylene) means an aromatic heterocycle that contains at least one ring heteroatom selected from N, O and S (including SO and $SO_2$). Heteroaryls can be fused to other heteroaryls or to other kinds of rings, such as aryls, cycloalkyls or heterocycles that are not aromatic. Examples of monocyclic heteroaryls and heteroaryls fused to other rings (aryl or heteroaryl) include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, dibenzofuran and the like.

"Halogen" includes fluorine, chlorine, bromine and iodine. Chlorine and fluorine are generally preferred.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Optical Isomers-Diastereomers-Geometric Isomers-Tautomers

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of Formula I.

Formula I shows the structure of the class of compounds without preferred stereochemistry. Formula Ia shows the preferred sterochemistry at the carbon atom that is attached to the amine group of the beta amino acid from which these compounds are made.

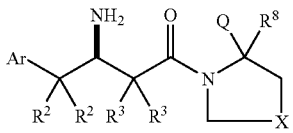

Formula Ib shows the preferred sterochemistry at the carbon atom that is attached to the amine group of the beta amino acid from which these compounds are made and at the carbon atom attached to substituent Q.

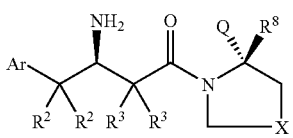

The various substituent groups in the compounds of Formula Ia and Ib are the same as those described previously for the compounds having Formula I.

If desired, racemic mixtures of compounds of Formula I may be separated so that the individual enantiomers are isolated. The separation can be carried out by methods well known in the art, such as the coupling of a racemic mixture of compounds of Formula I to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds of Formula I can also be separated directly by chromatographic methods utilizing chiral stationary phases, which methods are well known in the art.

Alternatively, any enantiomer of a compound of the general Formula I may be obtained by stereoselective synthesis using optically pure starting materials or reagents of known configuration. Such methods are well known in the art.

Compounds of Formula I may have more than one asymmetric center, as can be seen in Figure Ib. Such compounds may occur as mixtures of diasteromers, which can be separated into individual diasteromers by standard methods, and the diastereomers can be further separated to individual enantiomers as described above.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites-Prodrugs

Metabolites of the compounds of this invention that are therapeutically active and that are defined by Formula I or Ia are also within the scope of this invention. Prodrugs are compounds that are converted to therapeutically active compounds as they are being administered to a patient or after they have been administered to a patient. Prodrugs which are subsequently converted to a compound defined by Formula I during or after administration are also within the scope of the invention, as are the active metabolites of the prodrug. A non-limiting example of a prodrug of a compound having Formula I is a compound in which the amine group is functionalized with a group or groups that are removed under physiological conditions after administration to a mammalian patient to yield a compound having Formula I, or a pharmaceutically acceptable salt thereof.

Utilities

DP-IV is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides invitro. This has suggested a potential role for this peptidase in a variety of disease processes.

1. Type II Diabetes and Related Disorders

It is well established that the incretins GLP-1 and GIP are rapidly inactivated in vivo by DP-IV. Studies with DP-IV $^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP, glucagon). Inactivation of these peptides by DP-IV may also play a role in glucose homeostasis.

The DP-IV inhibitors of this invention therefore may have utility in the treatment of type II diabetes and in the treatment and prevention of the numerous conditions that often accompany Type II diabetes, including metabolic syndrome X, reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore some or all of these may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

2. Obesity

There is an expectation that DP-IV inhibitors may be useful for the treatment of obesity. This expectation is based on the observed inhibitory effects on food intake and gastric emptying of GLP-1 and GLP-2. Exogenous administration of GLP-1 in humans significantly decreases food intake and slows gastric emptying (Am. J. Physiol. 277, R910–R916 (1999)). ICV administration of GLP-1 in rats and mice also has profound effects on food intake (Nature Medicine 2, 1254–1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (Nature Medicine 6, 802–807 (2000)).

3. Growth Hormone Deficiency

DP-IV inhibition may be useful for the treatment of growth hormone deficiency, based on the hypothesis that growth-hormone releasing factor (GRP), a peptide that stimulates release of growth hormone from the anterior pituitary, is cleaved by the DP-IV enzyme in vivo (WO 00/56297). The following data provide evidence that GRF is an endogenous substrate: (1) GRF is efficiently cleaved in vitro to generate the inactive product GRF[3–44] (BBA 1122, 147–153 (1992)); (2) GRF is rapidly degraded in plasma to GRF[3–44]; this is prevented by the DP-IV inhibitor diprotin A; and (3) GRF[3–44] is found in the plasma of a human GRF transgenic pig (J. Clin. Invest. 83, 1533–1540 (1989)). Thus DP-IV inhibitors may be useful for the same spectrum of indications which have been considered in the case of Growth Hormone secretagogues.

4. Intestinal Injury

The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (Regulatory Peptides 90, 27–32 (2000)). Administration of GLP-2 results in increased small bowel mass in rodents and attenuates intestinal injury in rodent models of colitis and enteritis.

5. Immunosuppression

It has been suggested that DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation.

A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosupressants in animal models of transplantation and arthritis. Prodipine (Pro-Pro-diphenyl-phosphonate), an irreversible inhibitor of DP-IV, was shown to double cardiac allograft survival in rats from day 7 to day 14 (Transplantation 63, 1495–1500 (1997)). DP-IV inhibitors have been tested in collagen and alkyldiamine-induced arthritis in rats and showed a statistically significant attenuation of hind paw swelling in this model (Int. J. Immunopharmacology 19, 15–24 (1997), Immunopharmacology 40, 21–26 (1998)).

DP-IV is upregulated in a number of autoimmune diseases including rheumatoid arthritis, multiple sclerosis, Graves' disease, and Hashimoto's thyroiditis (Immunology Today 20, 367–375 (1999)).

6. HIV Infection

A number of chemokines which inhibit HIV cell entry are potential substrates for DP-IV (Immunology Today 20, 367–375 (1999)). In the case of SDF-1alpha, cleavage decreases antiviral activity (PNAS 95, 6331–6 (1998)). Thus, stabilization of SDF-1alpha through inhibition of DP-IV would be expected to decrease HIV infectivity.

7. Hematopoiesis

It has been suggested that DP-IV may be involved in hematopoiesis. A DP-IV inhibitor, Val-Boro-Pro, stimulates hematopoiesis in a mouse model of cyclophosphamide-induced neutropenia (WO 99/56753).

8. Neuronal Disorders

A number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m \sim 10^6$ M$^{-1}$ s$^{-1}$ or greater. In an electric shock jump test model of analgesia in rats, a DP-IV inhibitor showed a significant effect that was independent of the presence of exogenous endomorphin-2 (Brain Research 815, 278–286 (1999)).

9. Tumor Invasion and Metastasis

An increase or decrease in expression of several ectopeptidases including DP-IV has been observed during the transformation of normal cells to a malignant phenotype (J. Exp. Med. 190, 301–305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

10. Benign Prostatic Hypertrophy

Increased DP-IV activity was noted in prostate tissue from patients with BPH (Eur. J. Clin. Chem. Clin. Biochem 30, 333–338 (1992)).

11. Sperm Motility/Male Contraception

In seminal fluid, prostatosomes, prostate derived organelles important for sperm motility, possess very high levels of DP-IV activity (Eur. J. Clin. Chem. Clin. Biochem 30, 333–338 (1992)).

12. Gingivitis

DP-IV activity was found in gingival crevicular fluid and in some studies correlated with periodontal disease severity (Arch. Oral Biol. 37, 167–173 (1992)).

13. Osteoporosis

GIP receptors are present in osteoblasts.

It is therefore anticipated that the compounds of Formula I, Ia and Ib may have utility in treating one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated by inhibition of DP-IV, wherein said treatment comprises the administration to a human or mammalian patient of a therapeutically effective amount of a compound having Formula I, including pharmaceutically acceptable salts and prodrugs.

Combination Therapy

Compounds of Formula I may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DP-IV) inhibitors;

(b) insulin sensitizers including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues such as tolbutamide and glipizide, meglitinide, and related materials;

(e) α-glucosidase inhibitors (such as acarbose);

(f) glucagon receptor antagonists such as those disclosed in WO 98/04528, WO 99/01423, WO 00/39088, and WO 00/69810;

(g) GLP-1, GLP-1 mimetics, and GLP-1 receptor agonists such as those disclosed in WO00/42026 and WO00/59887;

(h) GIP, GIP mimetics such as those disclosed in WO00/58360, and GIP receptor agonists;

(i) PACAP, PACAP mimetics, and PACAP receptor 3 agonists such as those disclosed in WO 01/23420;

(j) cholesterol lowering agents such as (i) HMG-CoA reductase inhibitors (lovastatin, simvastatin, pravastatin, fluvastatin, atorvastatin, rivastatin, itavastatin, rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gernfibrozil, clofibrate, fenofibrate and bezafibrate), (v) PPARα/γ dual agonists, such as KRP-297, (vi) inhibitors of cholesterol absorption, such as for example ezetimibe and beta-sitosterol, (vii) acyl CoA:cholesterol acyltransferase inhibitors, such as for example avasimibe, and (viii) antioxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide Y5 inhibitors, and β$_3$ adrenergic receptor agonists;

(m) an ileal bile acid transporter inhibitor; and (n) agents intended for use in inflammatory conditions such as aspirin, non-steroidal anti-inflammatory drugs, glucocorticoids, azulfidine, and cyclo-oxygenase 2 selective inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, PPAR agonists, PTP-1B inhibitors, other DP-IV inhibitors, and anti-obesity compounds.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt or prodrug thereof as an active ingredient, as well as a pharmaceutically acceptable carrier. Optionally other therapeutic ingredients or other DP-IV inhibitors, or both, may be included in the pharmaceutical compositions as discussed previously. The term "pharmaceutically acceptable salts" refers to salts prepared from pharmaceutically acceptable non-toxic bases or acids, including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Assays: Measurement of Inhibition Constants

Inhibition constants were determined as follows. A continuous fluorometric assay was developed with the substrate Gly-Pro-AMC, which is cleaved by DP-IV to release the fluorescent AMC leaving group. The kinetic parameters that describe this reaction are as follows: $K_m$=50 µM; $k_{cat}$=75 s$^{-1}$; $k_{cat}/K_m$=1.5×10$^6$ M$^{-1}$s$^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 μM AMC is produced in 30 minutes at 25 degrees C. Unless otherwise indicated, the enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme.

The compounds described herein generally have inhibition constants of less than 10 μM. Preferred compounds have inhibition constants of less than 1 μM. Highly preferred compounds have inhibition constants of less than 300 nM.

To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

Synthetic Schemes

The compounds (I) of the present invention can be prepared from beta amino acid intermediates such as those of formula II and substituted heterocyclic intermediates such as those of formula III, using standard peptide coupling conditions followed by deprotection. The preparation of these intermediates is described in the following schemes.

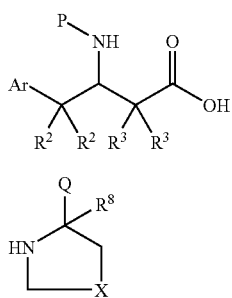

where Ar, $R^2$, $R^3$, $R^8$, Q, and X, are as defined above and P is a suitable nitrogen protecting group such as tert-butoxycarbonyl, benzyloxycarbonyl, or 9-fluorenylmethoxycarbonyl.

Compounds IIa, where $R^3$ is hydrogen, are commercially available, known in the literature or may be conveniently prepared by a variety of methods familiar to those skilled in the art. One common route is illustrated in Scheme 1. Acid 1, which may be commercially available or readily prepared from the corresponding amino acid by protection using, for example, N-(9-fluorenylmethoxycarbonyloxy)succinimide, is treated with isobutylchloroformate and diazomethane using a base such as triethylamine. The resultant diazoketone is then treated with silver benzoate in aqueous dioxane and may be subjected to sonication following the procedure of Sewald et al., *Synthesis*, 837 (1997) in order to provide the beta amino acid IIa. As will be understood by those skilled in the art, for the preparation of enantiomerically pure beta amino acids II, enantiomerically pure alpha amino acids 1 may be used. Alternate routes to these compounds can be found in the following reviews: E. Juaristi, *Enantioselective Synthesis of β-Amino Acids*, Ed., Wiley-VCH, New York: 1997, Juaristi et al., *Aldrichimica Acta*, 27, 3 (1994), Cole et al., *Tetrahedron*, 32, 9517 (1994).

SCHEME 1

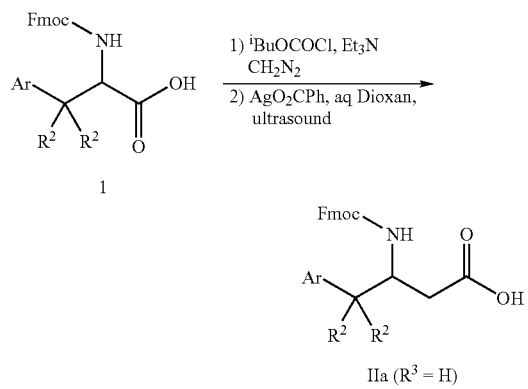

Compounds IIb, where $R^3$ is alkyl, may be conveniently prepared as described in Podlech et al., *Liebigs Ann*, 1217 (1995) and illustrated in Scheme 2. An amino acid such as IIa, from Scheme 1, can be esterified either by treatment with a mineral acid such as hydrochloric acid in an alcoholic solvent, for example methanol, at temperatures of 0 to 60° C. for 2 to 48 hours, or by using a coupling agent such as dicyclohexylcarbodiimide and an alcohol such as methanol or benzyl alcohol in dichloromethane. The resultant ester can then be deprotonated with a hindered base such as lithium diisopropylamide at a temperature of −80 to −60° C. and alkylated by addition of an alkyl halide such as methyl or ethyl iodide. Removal of the ester can then be achieved by treatment with a base such as aqueous lithium hydroxide in a solvent such as THF, methanol or mixture of similar solvents. In the case of a benzyl ester, removal is achieved by catalytic hydrogenation using a palladium catalyst in a solvent such as methanol, ethyl acetate or mixture of such solvents.

SCHEME 2

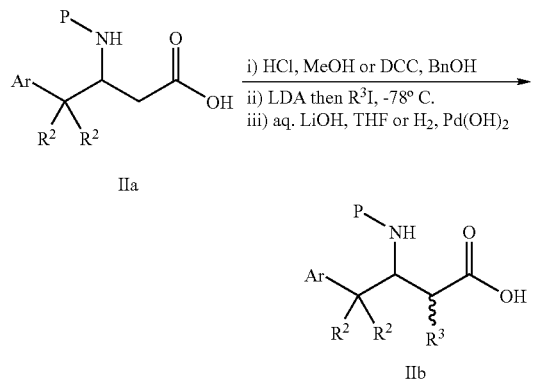

Compounds III are commercially available, known in the literature or may be conveniently prepared by a variety of methods familiar to those skilled in the art. A convenient route for their preparation when Q is CONR⁴Z is illustrated in Scheme 3. An amino acid 2 such as L-proline, alpha-methyl-L-proline or (R) 4-thiazolidinecarboxylic acid can be protected as a suitable carbamate derivative 3 with, for example, di-tert-butyldicarbonate or carbobenzyloxy chloride. This compound is then treated with an amine under standard peptide coupling conditions with, for example, 1-ethyl-3-(3-dimethylaminopropyl)carbodiimide (EDC), 1-hydroxybenzotriazole (HOBT), and a base, generally diisopropylethylamine, in a solvent such as N,N-dimethylformamide (DMF) for 3 to 48 hours at ambient temperature. The protecting group is then removed from compound 4 with, for example, trifluoroacetic acid in the case of Boc or catalytic hydrogenation in the case of Cbz, to give the desired amine IIIa, where $R^4$, $R^8$, and Z are as defined above.

hydroxide in a solvent such as dioxane. Removal of the protecting group as described above gives the product IIIb.

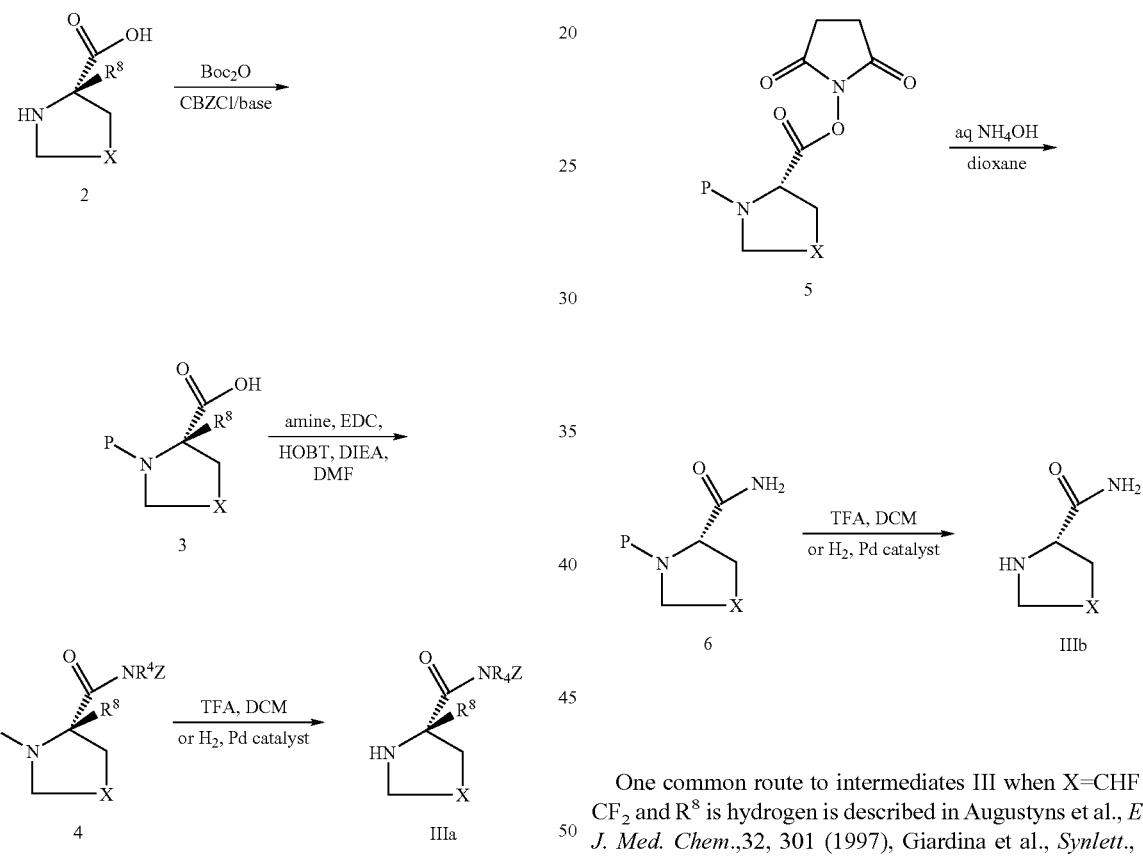

In some cases, the coupling product 4 from the reactions described in Scheme 3 may be further modified, for example, by the removal of protecting groups or manipulation of substituents on $NR^4Z$. These manipulations may include, but are not limited to, reduction, oxidation, alkylation, acylation, and hydrolysis reaction which are commonly known to those skilled in the art.

An alternate route to compounds III, which is particularly applicable when Q is a primary carboxamide and $R^8$ is hydrogen is illustrated in Scheme 4 and involves treatment of carbamate derivative 3 with N-hydroxysuccinimide and 1-ethyl-3-(3-dimethylaminopropyl)carbodiimide (EDC) or other suitable coupling agent in a solvent such as dichloromethane for 1 to 16 hours. The resulting product 5 is then treated with an amine, for example, aqueous ammonium One common route to intermediates III when X=CHF or $CF_2$ and $R^8$ is hydrogen is described in Augustyns et al., *Eur. J. Med. Chem.*, 32, 301 (1997), Giardina et al., *Synlett.*, 55 (1995), or Demange et al., *Tetrahedron Lett.*, 39, 1169 (1998) and illustrated in Scheme 5. Suitably protected alcohols 7 are commercially available, known in the literature or may be conveniently prepared by a variety of methods familiar to those skilled in the art. Treatment of 7 with a fluorinating agent such as diethylamino sulfur trifluoride in a solvent such as dichloromethane or benzene at −80 to 25° C. for 1 to 24 hours yields the corresponding fluoro derivative which may be deprotected as described above to give the desired amine IIIc. Alternatively, oxidation of alcohol 7 to the corresponding ketone 8 can be achieved by treatment with an oxidizing agent such as pyridinium dichromate in a solvent such as dichloromethane for up to 48 hours. Treatment of ketone 8 in a manner identical to that described above yields the difluoro amine IIId.

SCHEME 5

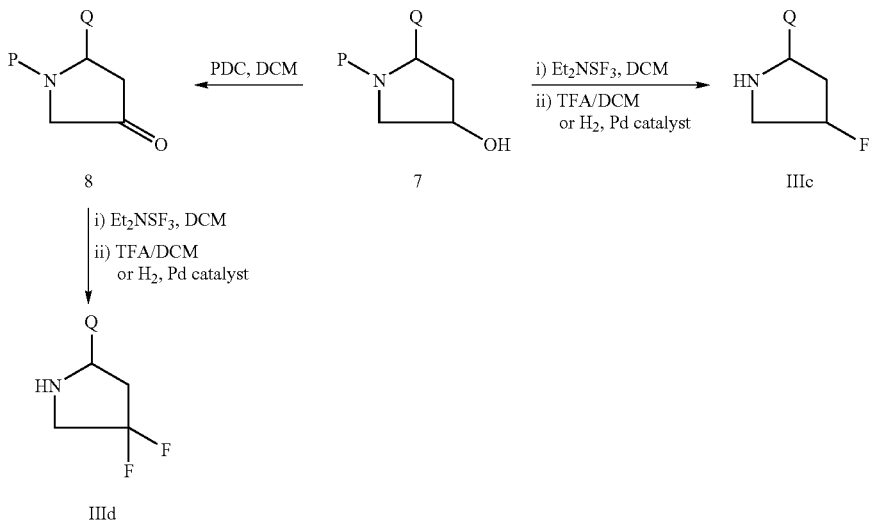

Intermediates II and III are coupled under standard peptide coupling conditions, for example, using 1-ethyl-3-(3-dimethylaminopropyl)carbodiimide (EDC), 1-hydroxybenzotriazole (HOBT), and a base, generally diisopropylethylamine, in a solvent such as N,N-dimethylformamide (DMF) or methylene chloride for 3 to 48 hours at ambient temperature to provide intermediate 9 as shown in Scheme 6. The protecting group is then removed with, for example, trifluoroacetic acid in the case of Boc to give the desired amine I. The product is purified from unwanted side products by recrystallization, trituration, preparative thin layer chromatography, flash chromatography on silica gel as described by W. C. Still et al, *J. Org. Chem.*, 43, 2923 (1978), or HPLC. Compounds which are purified by HPLC may be isolated as the corresponding salt. Purification of intermediates is achieved in the same manner.

SCHEME 6

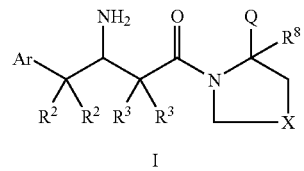

In some cases the intermediate 9 from the coupling reaction described in Scheme 6 may be further modified before removal of the protecting group, for example, by manipulation of substituents on Q. These manipulations may include, but are not limited to, reduction, oxidation, alkylation, acylation, and hydrolysis reactions which are commonly known to those skilled in the art. One such example is illustrated in Scheme 7. Compound 10, which is prepared as outlined in Scheme 6, is treated with a dehydrating agent such as cyanuric chloride in a polar solvent, for example, dimethylformamide for 1 to 16 hours at 0° C. to 50° C. to form the nitrile. Protecting group removal is then achieved as described above for compound 9 to give amine Ic.

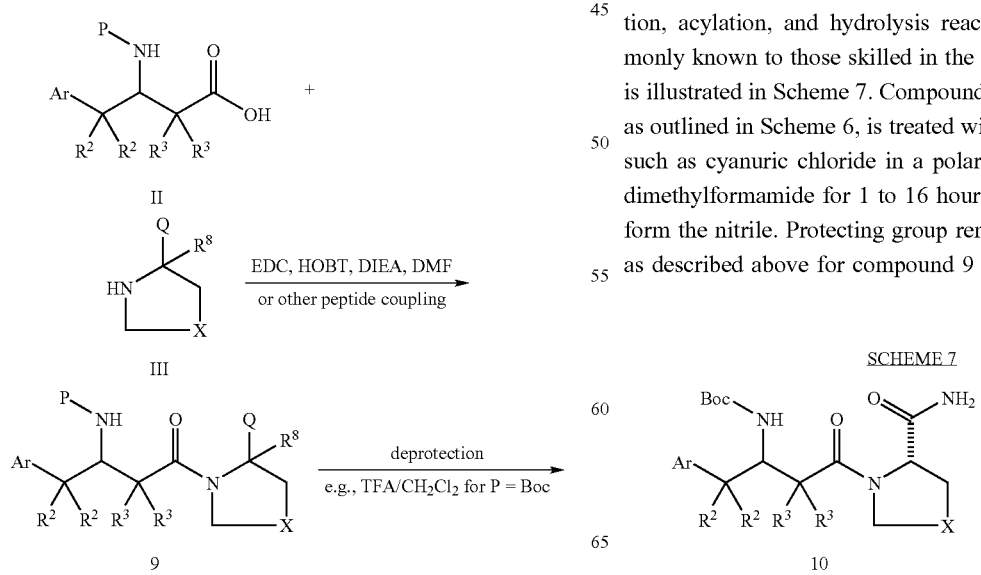

-continued

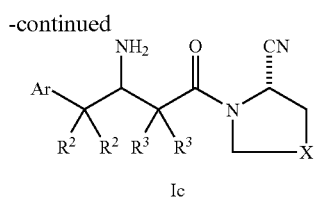

Ic

Another such example is shown in Scheme 8. The phenolic group in compound 11, prepared as described in Scheme 6, is alkylated with an alkyl halide, for example, methyl 2-bromoacetate using an inorganic base such as potassium carbonate in a polar solvent such as N,N-dimethylformamide to give intermediate 12. Removal of the protecting group with, in the case of a tert-butylcarbamate, an acid such as trifluoroacetic acid or methanolic hydrogen chloride, provides the product Id. In some cases, the coupling product 12 from the reaction described in Scheme 8 may be further modified, for example, by the removal of protecting groups or manipulation of substituents. These manipulations may include, but are not limited to, reduction, oxidation, alkylation, acylation, coupling and hydrolysis reactions which are commonly known to those skilled in the art.

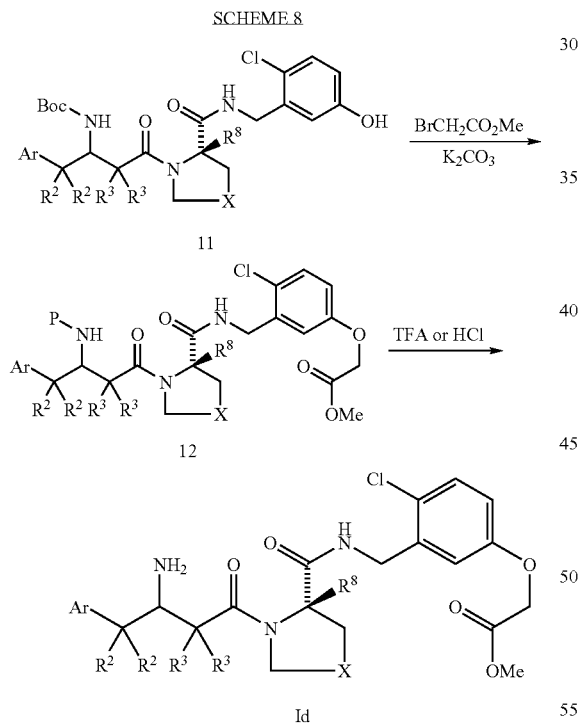

Another such example is shown in Scheme 9. The ester functionality in compound 13, prepared as described in Scheme 6, is removed to give carboxylic acid 14. In the case of an ester such as methyl or ethyl, this is achieved by saponification using a base such as aqueous lithium hydroxide in a polar solvent such as tetrahydrofuran, methanol or a mixture of similar solvents. Alternatively, if compound 13 contains a benzyl ester, removal is achieved by catalytic hydrogenation using a palladium catalyst in a solvent such as methylene chloride, ethyl acetate, methanol or mixture of such solvents which may contain a mineral acid such as hydrochloric acid in catalytic quantities. Compound 14 may then be coupled with an amine to give products such as amide 15. This coupling can be performed using standard peptide coupling conditions, for example, 1-ethyl-3-(3-dimethylaminopropyl)carbodiimide (EDC), 1-hydroxybenzotriazole (HOBT), and a base, generally diisopropylethylamine, in a solvent such as N,N-dimethylformamide (DMF) or methylene chloride for 3 to 48 hours at ambient temperature to provide intermediate 15. Removal of the protecting group with, in the case of a tert-butylcarbamate, an acid such as trifluoroacetic acid or methanolic hydrogen chloride, provides the compound Ie. In some cases there may be concomitant removal of other acid labile functionality in the molecule. For example if $NR^4Z$ contains a tert-butyl ester moiety, then it may be converted to a carboxylic acid in product Ie.

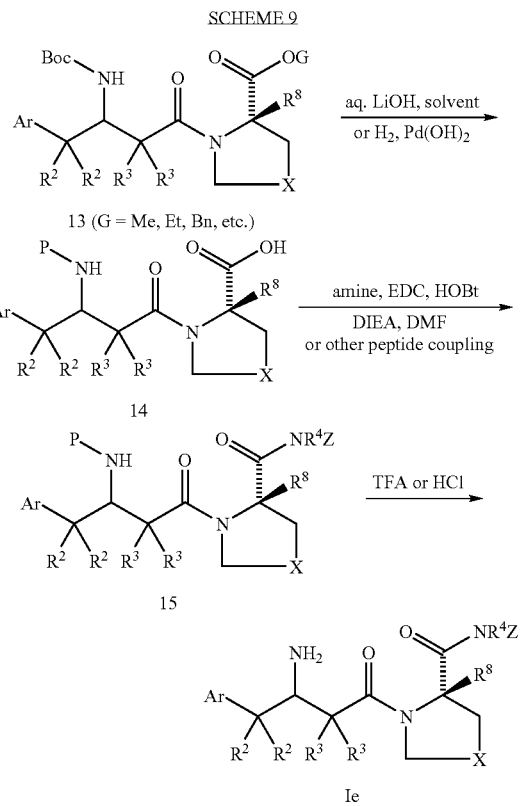

In some cases, the coupling product 15 from the reaction described in Scheme 9 may be further modified, for example, by the removal of protecting groups or manipulation of substituents on $NR^4Z$. These manipulations may include, but are not limited to, reduction, oxidation, alkylation, acylation, and hydrolysis reactions which are commonly known to those skilled in the art.

Another such example is illustrated in Scheme 10. Compound 16 is prepared as described in Scheme 6 using a beta amino acid II where $R^3=OP^1$ ($P^1$ being a suitable protecting group such as tert-butyldimethylsilyl). Such amino acids are commercially available, known in the literature or may be conveniently prepared by a variety of methods familiar to those skilled in the art. Compound 16 is then treated with a fluoride source such as tetrabutylammonium fluoride in a solvent, normally THF, for 2 to 48 hours to release the alcohol 17. This is then subsequently reacted with a fluorinating agent such as [bis(2-methoxyethyl)amino]sulfur trifluoride followed by removal of the protecting group as previously described to give the fluoro analog If.

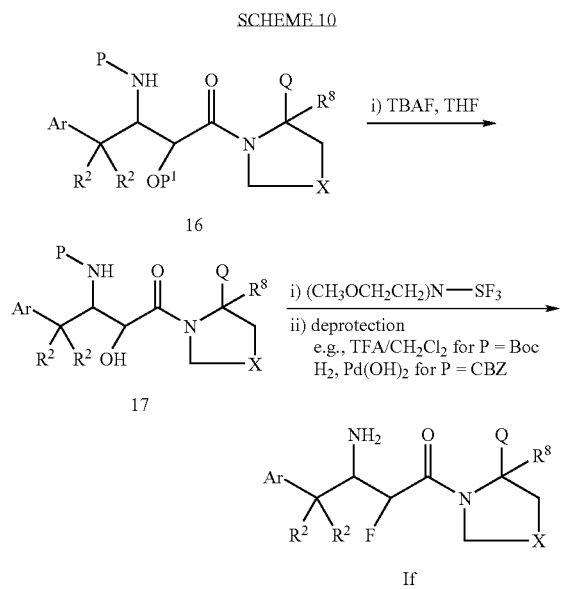

SCHEME 10

Compound Ig, where X is CHC(O)NR⁴Z and Q and R⁸ are hydrogen, may be prepared as illustrated in Scheme 11. Intermediate II and pyrrolidine-3-carboxylic acid, suitably protected, for example, as its benzyl ester 18, are coupled under standard peptide coupling conditions, for example, using 1-ethyl-3-(3-dimethylaminopropyl)carbodiimide (EDC), 1-hydroxybenzotriazole (HOBT), and a base, generally triethylamine or diisopropylethylamine, in a solvent such as N,N-dimethylformamide (DMF), tetrahydrofuran (THF) or methylene chloride for 3 to 48 hours at ambient temperature to provide intermediate 19. The ester is then removed. In the case of a benzyl ester, this may be readily achieved by treatment with hydrogen in the presence of a catalyst such as 10% palladium on carbon in a solvent such as methanol or ethyl acetate. The resultant acid 20 is coupled to the requisite amine 21 to provide amide 22. The nitrogen protecting group is then removed with, for example, trifluoroacetic acid in the case of Boc, to give the desired amine Ig.

SCHEME 11

In some cases, the coupling product 22 or amine Ie from the reactions described in Scheme 11 may be further modified, for example, by the removal of protecting groups or manipulation of substituents on NR⁴Z. These manipulations may include, but are not limited to, reduction, oxidation, alkylation, acylation, and hydrolysis reactions which are commonly known to those skilled in the art.

EXAMPLES

The following examples are provided so that the invention might be more fully understood. These exampes are illustrative only and should not be construed as limiting the invention in any way.

Example 1

Step A. 5-Chloro-2-hydroxybenzylamine. To 1.56 g (0.01 mol) of 5-chlorosalicaldehyde in 14 mL of a 1:1 mixture of ethanol:pyridine was added 0.834 g (0.012 mol) of hydroxylamine hydrochloride. The mixture was heated at 80° C. for 16 h, cooled and concentrated in vacuo. Water was added and the mixture was extracted three times with methylene chloride. The combined organic phase was washed with brine, dried over magnesium sulfate, and concentrated in vacuo. The crude material was dissolved in 30 mL of ethanol and 5 g (0.76 mol) of zinc, 0.638 g (0.083 mol) of ammonium acetate, and 69 mL of 30% aqueous ammonium hydroxide solution were added. The mixture was heated at 100° C. for 16 h, cooled and concentrated in vacuo. Water was added and the mixture was filtered through a Celite pad and extracted three times with ethyl acetate. The combined organic phase was washed with brine, dried over magnesium sulfate, and concentrated in vacuo to give 930 mg of the title compound which was used without further purification. $^1$H NMR (400 MHz, CD$_3$OD) δ 7.10 (m, 2H), 6.75 (d, 1H, J=8 Hz), 3.93 (s, 2H).

Step B. tert-Butyl (2S)-2-[(5-chloro-2-hydroxyphenyl)acetyl]pyrrolidine-1-carboxylate. To a solution of 0.93 g (5.9 mmol) of 5-chloro-2-hydroxybenzylamine in 20 mL of dimethylformamide (DMF) was added 1 g (4.2 mmol) of N-Boc-L-proline, 1.08 g (5.6 mmol) of 1-ethyl-3-(3-dimethylaminopropyl)carbodiimide hydrochloride (EDC), 940 mg (6.9 mmol) of 1-hydroxybenzotriazole hydrate (HOBT), and 2.02 mL (11.5 mmol) of diisopropylethylamine (DIEA). The mixture was stirred for 16 h and diluted with ethyl acetate. The organic phase was washed sequentially with water, saturated aqueous sodium bicarbonate solution, water, and brine, dried over magnesium sulfate and the solvent removed in vacuo to yield 1.7 g of residue which was immediately dissolved in 15 mL of THF. To this solution was added 650 mg (15 mmol) of lithium hydroxide in 15 mL of water and the reaction was stirred for 16 h and concentrated in vacuo. The aqueous solution was acidified with 2N hydrochloric acid and extracted three times with ethyl acetate. The combined organic phase was washed with brine, dried over magnesium sulfate, and concentrated in vacuo to give 1.24 g of product. Purification by flash chromatography (silica gel, 33 to 50% ethyl acetate in hexanes) afforded 0.82 g of the title compound. $^1$H NMR (400 MHz, CD$_3$OD) δ 7.18 (s, 1H), 7.03 (m, 1H), 6.73 (m, 1H), 4.38–4.12 (m, 3H), 3.56–3.46 (m, 2H), 2.3–1.8 (m, 4H), 1.5–1.25 (m, 9H).

Step C. 1-{(3R)-3-[(tert-Butoxycarbonyl)amino]-4-phenylbutanoyl}-N-(5-chloro-2-hydroxybenzyl)-L-prolinamide. To a solution of 0.1 g (0.28 mmol) of tert-butyl (2S)-2-[(5-chloro-2-hydroxyphenyl)acetyl]pyrrolidine-1-carboxylate in 2 mL of methylene chloride was added 2 mL of trifluorocetic acid. The solution was stirred at ambient temperature for 2 h, the solvent removed in vacuo and the residual oil dissolved in methylene chloride and concentrated to remove excess trifluoroacetic acid. The product was dissolved in 1 mL of DMF and to this solution was added 78 mg (0.28 mmol) of N-BOC-(R)-beta-phenylalanine, 66 mg (0.33 mmol) of 1-ethyl-3-(3-dimethylaminopropyl)-carbodiimide hydrochloride (EDC), 57 mg (0.42 mmol) of 1-hydroxybenzotriazole hydrate (HOBT), and 0.246 mL (1.4 mmol) of diisopropylethylamine (DIEA). The mixture was stirred for 16 h and diluted with ethyl acetate. The organic phase was washed sequentially with water, saturated aqueous sodium bicarbonate solution, water, and brine, dried over magnesium sulfate and the solvent removed in vacuo to yield 141 mg of the title compound.

Step D. 1-[(3R)-3-Amino-4-phenylbutanoyl]-N-(5-chloro-2-hydroxybenzyl)-L-prolinamide. A portion (18 mg) of product from Step C was deprotected by treatment with trifluoroacetic acid as described above, followed by purification using preparative thin layer chromatography (TLC) (silica gel, 9:1:90 methanol:concentrated ammonium hydroxide:methylene chloride) to give 9 mg of the title compound. $^1$H NMR (400 MHz, CD$_3$OD) δ 7.35–7.00 (m, 7H), 6.79 (d, 0.25H, J=8 Hz), 6.71 (d, 0.75H, J=8 Hz), 4.45–4.23 (m, 3H), 3.6–3.38 (m, 3H), 2.81–2.52 (m, 3H), 2.40–2.10 (m, 2H), 2.07–1.80 (m, 3H).

Example 2

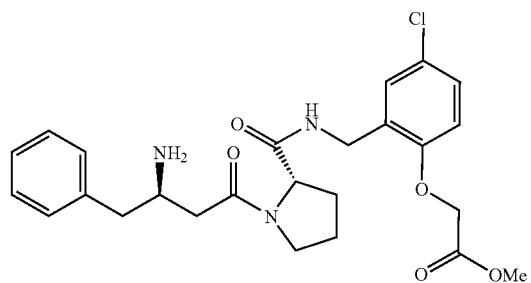

Methyl {2-[({1-[(3R)-3-amino-4-phenylbutanoyl]-L-prolyl}amino)methyl]-4-chlorophenoxyacetate. To 120 mg (0.23 mmol) of 1-{(3R)-3-[(tert-butoxycarbonyl)amino]-4-phenylbutanoyl}-N-(5-chloro-2-hydroxybenzyl)-L-prolinamide dissolved in 2 mL of DMF was added 193 mg (1.4 mmol) of potassium carbonate and 0.032 mL (0.33 mmol) of methyl bromoacetate. The reaction was stirred for 16 h at ambient temperature, diluted with ethyl acetate, washed sequentially with water and brine, dried with magnesium sulfate, and concentrated in vacuo to give 250 mg crude material. Purification by preparative TLC (silica gel, 1:1 ethyl acetate:hexanes) yielded 100 mg of the title compound as its tert-butyl carbamate.

A portion (19 mg) of this material was deprotected as described in Example 1, Step D, to give 14 mg of the title compound. $^1$H NMR (400 MHz, CD$_3$OD) δ 7.33–7.15 (m, 7H), 6.92 (d, 0.17H, J=8 Hz), 6.82 (d, 0.83H, J=8 Hz), 4.82 (s, 0.34H), 4.78 (s, 1.66H), 4.46–4.30 (m, 3H), 3.79 (s, 0.48H), 3.77 (s, 2.52H), 3.62–3.38 (m, 3H), 2.81–2.56 (m, 3H), 2.40–2.12 (m, 2H), 2.07–1.81 (m, 3H).

Example 3

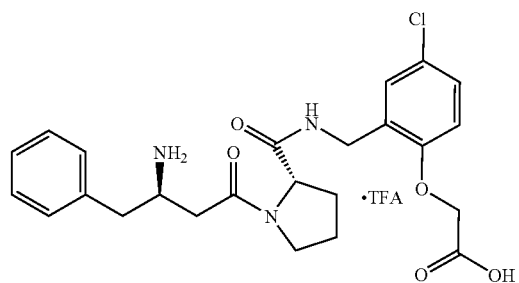

{2-[({1-[(3R)-3-Amino-4-phenylbutanoyl]-L-prolyl}amino)methyl]-4-chlorophenoxyacetic acid, trifluoroacetate salt. To a solution of 79 mg (0.135 mmol) of the tert butyl carbamate of methyl {2-[({1-[(3R)-3-amino-4-phenylbutanoyl]-L-prolyl}amino)methyl]-4-chlorophenoxyacetate in 1 mL of THF was added 28 mg (0.67 mmol) of lithium hydroxide in 1 mL of water and the reaction was stirred for 16 h and concentrated in vacuo. The aqueous solution was acidified with 2N hydrochloric acid and extracted three times with ethyl acetate. The combined organic phase was washed with brine, dried over magnesium sulfate, and concentrated in vacuo to give 71 mg of the title compound as its tert-butyl carbamate.

A portion (22 mg) of this material was deprotected as described in Example 1, Step D, followed by purification by preparative HPLC (10–50% acetonitrile in water containing 0.1% trifluoroacetic acid) to give 16 mg of the title compound. $^1$H NMR (400 MHz, CD$_3$OD) δ 7.40–7.08 (m, 7H), 6.95 (d, 0.2H, J=8 Hz), 6.86 (d, 0.8H, J=8 Hz), 4.80 (s, 0.4H), 4.73(s, 1.6H), 4.46–4.29 (m, 3H), 3.85–3.75 (m, 1H), 3.56–3.38 (m, 2H), 3.06–2.91 (m, 2H), 2.81–2.50 (m, 2H), 2.35–2.15 (m, 1H), 2.07–1.8 (m, 3H).

Example 4

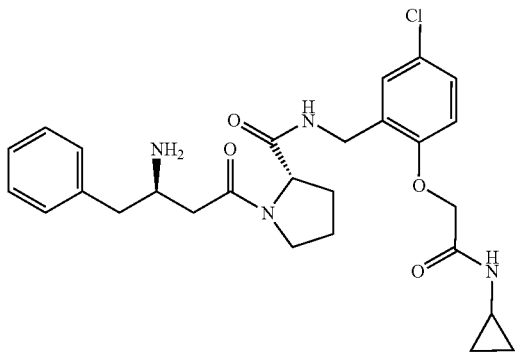

1-[(3R)-3-Amino-4-phenylbutanoyl]-N-{5-chloro-2-[2-(cyclopropylamino)-2-oxoethoxy]benzyl}-L-prolinamide. A solution of 46 mg (0.08 mmol) of the tert butyl carbamate of {2-[({1-[(3R)-3-amino-4-phenylbutanoyl]-L-prolyl}amino) methyl]-4-chlorophenoxyacetic acid and 0.0055 mL (0.096 mmol) of cyclopropylamine in DMF were coupled and deprotected as described for Example 1, Step C and D to give 25 mg of the title compound. $^1$H NMR (400 MHz, CD$_3$OD) δ 7.32–7.10 (m, 7H), 6.95 (d, 0.2H, J=8 Hz), 6.85 (d, 0.8H, J=8 Hz), 4.55–4.22 (m, 5H), 3.61–3.35 (m, 3H), 2.82–2.50 (m, 4H), 2.38–2.10 (m, 2H), 2.07–1.80 (m, 3H), 0.75–0.58 (m, 4H).

Example 5

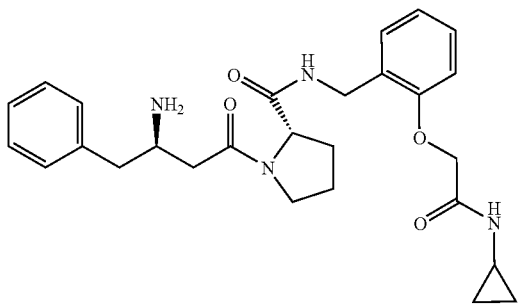

1-[(3R)-3-Amino-4-phenylbutanoyl]-N-{2-[2-(cyclopropylamino)-2-oxoethoxy]benzyl}-L-prolinamide. Palladium hydroxide on activated charcoal (~50 mg) was added to a solution of 15 mg of 1-[(3R)-3-amino-4-phenylbutanoyl]-N-{5-chloro-2-[2-(cyclopropylamino)-2-oxoethoxy]benzyl}-L-prolinamide in 1 mL methanol and the mixture was stirred under a balloon of hydrogen for 6 h. The reaction was diluted with methanol, filtered through a pad of Celite, and concentrated in vacuo. Purification using preparative TLC (silica gel, 13.5:1.5:85 methanol:concentrated ammonium hydroxide:methylene chloride) afforded 10 mg of the title compound. $^1$H NMR (400 MHz, CD$_3$OD) δ 7.33–7.10 (m, 7H), 7.01–6.83 (d, 2H), 4.58–4.22 (m, 5H), 3.61–3.35 (m, 3H), 2.84–2.48 (m, 4H), 2.38–2.08 (m, 2H), 2.05–1.80 (m, 3H), 0.78–0.60 (m, 4H).

Example 6

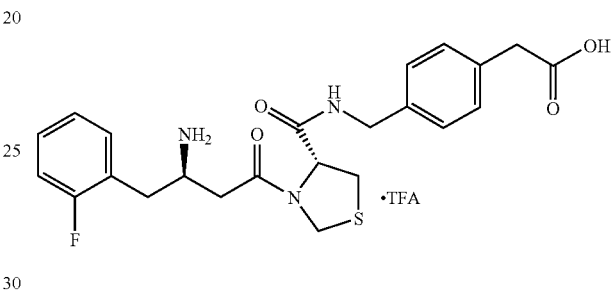

Step A. (4R)-3-[(3R)-3-[(tert-Butoxycarbonyl)amino]-4-(2-fluorophenyl)butanoyl]-1,3-thiazolidine-4-carboxylic acid. To a solution of 1.42 g (5.09 mmol) of (3R)-3-[(tert-butoxycarbonyl)amino]-4-(2-fluorophenyl)butanoic acid and 824 mg (5.6 mmol) of (R)-thiazolidine-4-carboxylic acid methyl ester in 20 mL of dichloromethane was added 1.02 g (5.34 mmol) of 1-ethyl-3-(3-dimethylaminopropyl) carbodiimide hydrochloride (EDC), 688 mg (5.1 mmol) of 1-hydroxybenzotriazole hydrate (HOBT), and 0.93 mL (5.34 mmol) of diisopropylethylamine (DIEA). The mixture was stirred for 16 h and diluted with dichloromethane. The organic phase was washed sequentially with 10% hydrochloric acid, sodium carbonate solution, and brine, dried over sodium sulfate and the solvent removed in vacuo. The product was purified by Biotage chromatography (silica gel, 30–60% ethyl acetate in hexanes) to give 0.59 g of coupled material. This material was dissolved in 28 mL of a 3:1 mixture of THF:methanol and 6.9 mL of 1N aqueous lithium hydroxide solution was added. The reaction was stirred for 1 h and concentrated, acidified with 10% hydrochloric acid, and extracted twice with dichloromethane. The combined organic layers were washed with brine, dried with sodium sulfate, and concentrated in vacuo to give 450 mg of the title compound. $^1$H NMR (500 MHz, CD$_3$OD) δ 7.31–7.18 (m, 2H), 7.11–6.98 (m, 2H), 5.05–4.93 and 4.90–4.85 (m, 1H), 4.78–4.57 (m, 1.6H), 4.45 (t, 0.4H, J=10 Hz), 4.30–4.18 (m, 1H), 3.41–3.30 (m, 1.4H), 3.23–3.20 (m, 0.6H), 3.02–2.42 (m, 4H), 1.40–1.22 m, 9H).

Step B (2R)-4-[(4R)-4-({[4-Carboxymethyl)benzyl] amino}carbonyl)-1,3-thiazolidin-3-yl]-1-(2-fluorophenyl)-4-oxobutan-2-amine, trifluoroacetate salt. Using the coupling procedure described in Example 6 Step A, 50 mg (0.12 mmol) of (4R)-3-[(3R)-3-[(tert-butoxycarbonyl)amino)]-4-(2-fluorophenyl)butanoyl]-1,3-thiazolidine-4-carboxylic acid was coupled with 47 mg (0.15 mmol) of the oxalate salt of 2-(4-aminomethylphenyl)acetic acid tert-butyl ester. The resultant amide was treated with 4 mL of a 1:1:0.1 mixture of methylene chloride: trifluoroacetic acid: methyl sulfide at ambient temperature for 1 hour and concentrated. The crude product was purified by reverse phase preparative HPLC (10–65% acetonitrile in water containing 0.1% trifluoroacetic acid) to give 38 mg of the title compound. $^1$H NMR (500 MHz, CD$_3$OD) δ 7.39–7.10 (m, 8H), 4.91–4.60 (m, 2H), 4.58–4.50 (m, 1H), 4.43–4.20 (m,2H), 3.91–3.78 (m, 1H), 3.60–3.56 (m, 2H), 3.43–3.25 (m, 1H), 3.20–2.90 (m, 3H), 2.90–2.68 (m, 2H).

Example 7

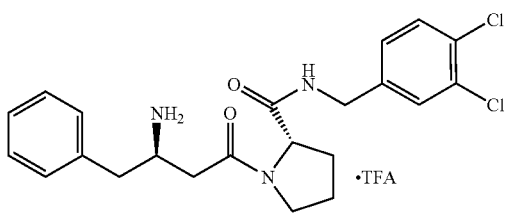

Step A. 1-[(tert-Butoxycarbonyl)-N-(3,4-dichlorobenzyl)-L-prolinamide. To a solution of 0.768 mL (5.76 mmol) of 3,4-dichlorobenzylamine in 20 mL of dimethylformamide (DMF) was added 1.24 g (5.76 mmol) of N-BOC-L-proline, 1.21 g (6.3 mmol) of 1-ethyl-3-(3-dimethylaminopropyl) carbodiimide hydrochloride (EDC), 856 mg (6.3 mmol) of 1-hydroxybenzotriazole hydrate (HOBT), and 2 mL (11.52 mmol) of diisopropylethylamine (DIEA). The mixture was stirred for 16 h and diluted with ethyl acetate. The organic phase was washed sequentially with water, saturated aqueous sodium bicarbonate solution, water, brine, dried over magnesium sulfate and the solvent removed in vacuo to yield a crude mixture which was purified by flash chromatography (silica gel, 1:1 hexanes:ethyl acetate) to yield 1.61 g of the title compound. $^1$H NMR (500 MHz, CDCl$_3$) δ 7.61 (s, 1H), 7.38–7.12 (m, 7 H), 5.24 (s, 1H), 4.60 (m, 1H), 4.41 (m, 2H), 4.18 (m, 1H), 3.40 (m, 1H), 3.18(m, 1H), 2.98 (m, 1H), 2.81 (m, 1H), 2.41 (m, 2H), 2.38 (m, 1H), 2.05 (m, 2H), 1.98 (m, 2H), 1.40 (s, 9H).

Step B. 1-[(3R)-3-Amino-4-phenylbutanoyl]-N-(3,4-dichlorobenzyl)-L-prolinamide, trifluoroacetate salt. The title compound was prepared from 1-[(tert-butoxycarbonyl)-N-(3,4-dichlorobenzyl)-L-prolinamide in a manner identical to that described in Example 1, Step C and D and was isolated as the trifluoroacetate salt without further purification. $^1$H NMR (500 MHz, CDCl$_3$) δ 7.34 (m, 2H), 7.31 (m, 2H), 7.21 (m, 1H), 7.18 (m, 2H), 7.10 (m, 1H), 4.42 (m, 2H), 3.80 (m, 1H), 3.58 (m, 1H), 2.99 (m, 1H), 2.78 (m, 1H), 2.60 (m, 1H), 2.21 (m, 1H), 1.98 (m, 2H), 1.30 (m, 4H).

Following the procedures outlined for Examples 1–7, the compounds listed in Tables 1 and 2 were prepared

TABLE 1

| Example | Ar | X | R | Selected $^1$H NMR data |
|---|---|---|---|---|
| 8 | Ph | S | ![structure: 4-Cl-phenyl with -CH$_2$OC(O)OH substituent] | TFA salt: 7.40–7.18(m, 7H), 6.94–6.85(m, 1H), 4.8–4.65(m, 3H), 4.45–4.39 (m, 2H) |
| 9 | Ph | CH$_2$ | ![structure: 4-Cl-phenyl with -CH$_2$OC(O)OH substituent] | TFA salt: 7.40–7.18(m, 5H), 7.13(dd, 0.25H, J = 8.6, 2.5 Hz), 7.10–7.01(m, 1H), 6.98(d, 0.75H, J = 9 Hz), 4.78–4.57(m, 3H) |

TABLE 1-continued

| Example | Ar | X | R | Selected ¹H NMR data |
|---|---|---|---|---|
| 10 | Ph | $CH_2$ | 2-(carboxymethyl)benzyl | TFA salt: 7.4–7.1(m, 9H), 3.83–3.7(m, 3H) |
| 11 | Ph | S | 2-(methoxycarbonylmethyl)benzyl | TFA salt: 7.39–7.18(m, 9H), 3.83–3.75(m, 3H), 3.69–3.63(m, 3H) |
| 12 | Ph | $CH_2$ | 3-(carboxymethyl)benzyl | TFA salt: 7.39–7.13(m, 9H), 3.60(s, 0.66H), 3.56(s, 1.34H) |
| 13 | Ph | S | 3-(methoxycarbonylmethyl)benzyl | TFA salt: 7.39–7.13(m, 9H), 3.84–3.72(m, 3H), 3.68–3.62(m, 5H) |
| 14 | Ph | $CH_2$ | 4-(carboxymethyl)benzyl | TFA salt: 7.40–7.15(m, 9H), 3.57(s, 0.66H), 3.56(s, 1.34H) |
| 15 | Ph | S | 4-(carboxymethyl)benzyl | TFA salt: 7.40–7.18(m, 9H), 3.59–3.56(m, 2H) |
| 16 | Ph | $CH_2$ | 4-carboxybutyl | TFA salt: 3.28–3.10(m, 2H), 2.38–2.25(m, 2H), 1.85–1.73(m, 2H) |
| 17 | Ph | $CH_2$ | 5-carboxypentyl | TFA salt: 3.28–3.15(m, 2H), 2.38–2.25(m, 2H), 1.64–1.50(m, 4H) |

TABLE 1-continued
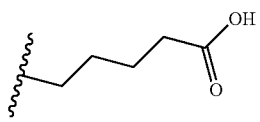
| Example | Ar | X | R | Selected ¹H NMR data |
|---|---|---|---|---|
| 18 | Ph | S | 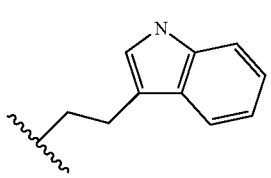 | TFA salt: 3.28–3.18(m, 2H), 2.35–2.25(m, 2H), 1.62–1.40(m, 4H) |
| 19 | Ph | CH₃ | 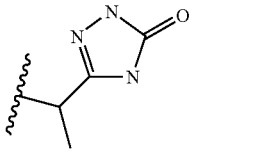 | TFA salt: 7.58(d, 0.25H, J = 8 Hz), 7.55(d, 0.75H, J = 8 Hz), 7.38–7.12(m, 5H), 7.05(m, 2H), 7.02–6.96(m, 1H), 3.6–3.32(m, 4H), 3.05–2.79(m, 4H) |
| 20 | Ph | CH₂ | 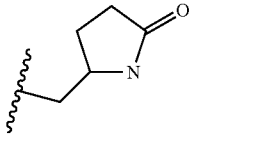 | TFA salt: 4.90–4.80(m, 1H), 1.46(d, 3H, J = 7 Hz) |
| 21 | Ph | CH₂ | 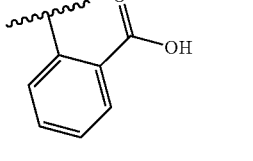 | TFA salt: 3.88–3.72(m, 2H), 3.5–3.4(m, 3H), 3.2–2.92(m, 3H), 2.78–2.50(m, 2H), 2.43–2.17(m, 4H), 2.05–1.80(m, 4H) |
| 22 | Ph | CH₂ | 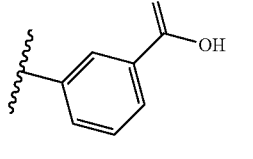 | TFA salt: 7.59–7.12(m, 9H) |
| 23 | Ph | CH₂ | 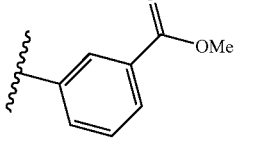 | TFA salt: 7.82–7.75(m, 2H), 7.50–7.18(m, 7H) |
| 24 | Ph | CH₂ | 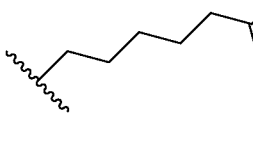 | TFA salt: 3.91(s, 0.5H), 3.88(s, 2.5H) |
| 25 | Ph | CH₂ |  | TFA salt: 3.20–3.10(m, 2H), 2.34–2.24(m, 2H), 1.64–1.58(m, 2H), 1.55–1.48(m, 2H), 1.40–1.32(m, 2H) |

TABLE 1-continued
| Example | Ar | X | R | Selected $^1$H NMR data |
|---|---|---|---|---|
| 26 | Ph | CH$_2$ | 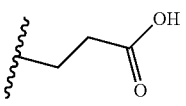 | TFA salt: 3.65(s, 0.55H), 3.64(s, 2.45H) |
| 27 | Ph | CH$_2$ | 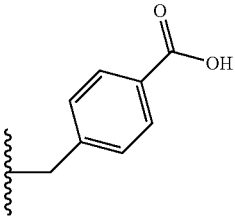 | TFA salt: 3.53–3.38(m, 4H), 2.49(t, 2H, J = 6.7 Hz) |
| 28 | Ph | CH$_2$ | 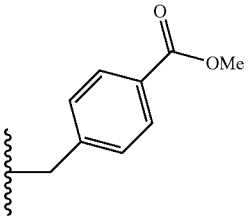 | TFA salt: 8.05–7.95(m, 2H), 7.41–7.26(m, 6.5H), 7.19–7.17(m, 0.5H), 4.52–4.28 (m, 4H) |
| 29 | Ph | CH$_2$ | 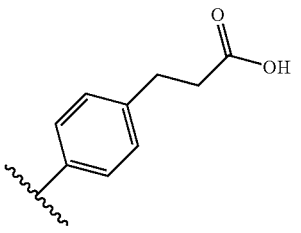 | TFA salt: 3.88(s, 0.47H), 3.87(s, 2.53H) |
| 30 | Ph | CH$_2$ | 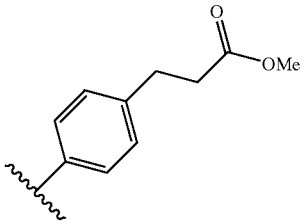 | TFA salt: 7.46(d, 0.5H, J = 8.5 Hz), 7.44(s, 1.5H, J = 8.5 Hz), 7.40–7.21(m, 5H), 7.17(d, 2H, J = 8.5 Hz), 2.87(t, 2H, J '2 7.5 Hz), 2.60–2.54(m, 3H) |
| 31 | Ph | CH$_2$ | 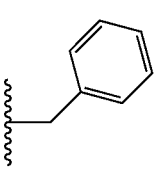 | TFA salt: 3.63(s, 0.58H), 3.62(s, 2.42H) |
| 32 | Ph | CH$_2$ |  | TFA salt: 7.38–7.25(m, 9H), 7.24–7.25(m, 1H), 4.39(bs, 0.2H), 4.37(bs, 1.8H) |

TABLE 1-continued
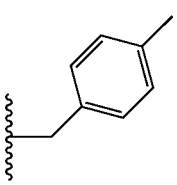
| Example | Ar | X | R | Selected ¹H NMR data |
|---|---|---|---|---|
| 33 | Ph | CH$_2$ | 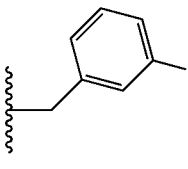 | TFA salt: 7.39–7.27(m, 5H), 7.20–7.07(m, 4H), 4.31(s, 2H), 2.23(s, 0.6H), 2.27(s, 2.4H) |
| 34 | Ph | CH$_2$ | 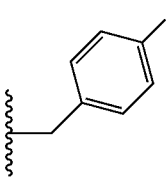 | TFA salt: 7.37–7.27(m, 5H), 7.19(t, 1H, J = 7.8 Hz), 6.89–6.81(m, 2H), 6.77(dd, 1H, J = = 2, 8 Hz), 4.39–4.26(m, 2H), 3.77(s, 0.5H), 3.76(s, 2.5H) |
| 35 | Ph | CH$_2$ | 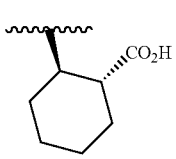 | TFA salt: 7.39–7.25(m, 5H), 7.23–7.18(m, 2H), 6.90(d, 0.36H, J = 8.7 Hz), 6.84(d, 1.64H, J = 8.7 Hz), 3.76(s, 0.6H), 3.75 (s, 2.4H) |
| 36 | Ph | CH$_2$ | 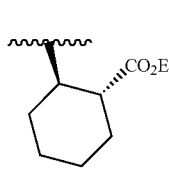<br>mixture of diastereomers | TFA salt: 3.95–3.87(m, 1H), 2.40–2.20(m, 1H), 2.02–1.70(m, 7H), 1.57–1.45(m, 1H), 1.42–1.20(m, 3H) |
| 37 | Ph | CH$_2$ | 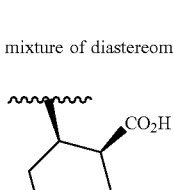<br>mixture of diastereomers | TFA salt: 4.13–4.01(m, 2H), 1.40–1.19(m, 6H) |
| 38 | Ph | CH$_2$ | 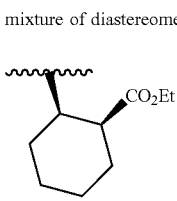<br>mixture of diastereomers | TFA salt: 4.29–4.19(m, 1H), 2.78–2.70(m, 1.75H), 2.04–1.88(m, 5H), 1.61–1.50(m, 4H), 1.50–1.38(m, 2H) |
| 39 | Ph | CH$_2$ |  | TFA salt: 4.12–4.00(m, 2H), 1.30–1.17(m, 3H) |

TABLE 1-continued
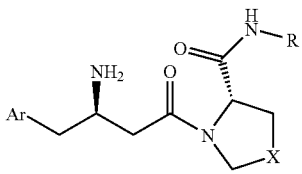
| Example | Ar | X | R | Selected $^1$H NMR data |
|---|---|---|---|---|
| | | | mixture of diastereomers | |
| 40 | Ph | CH$_2$ | 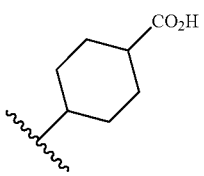 | TFA salt: 3.83–3.75(m, 2H), 2.57–2.45(m, 2H), 2.05–1.80(m, 5H), 1.73–1.20(m, 6H), |
| | | | mixture of diastereomers | |
| 41 | Ph | CH$_2$ | 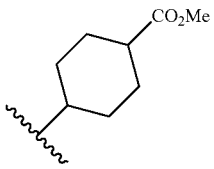 | TFA salt: 3.69(s, 0.75H), 3.66(s, 1.5H), 3.64(s, 0.75H) |
| | | | mixture of diastereomers | |
| 42 | Ph | CH$_2$ | 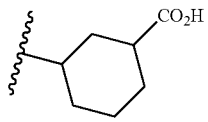 | TFA salt: 3.71–3.53(m, 1H), 2.40–2.33(m, 1H), 2.21–1.80(m, 8H), 1.43–1.12 (m, 4H), |
| | | | mixture of diastereomers | |
| 43 | Ph | CH$_2$ | 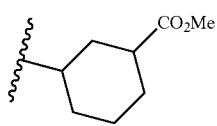 | TFA salt: 3.68–3.55(m, 4H) |
| | | | mixture of diastereomers | |
| 44 | Ph | CH$_2$ | 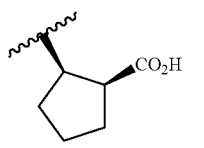 | TFA salt: 4.45–4.23(m, 2H), 3.09–2.84(m, 3H), 2.33–1.58(m, 10H) |
| | | | mixture of diastereomers | |
| 45 | Ph | CH$_2$ | 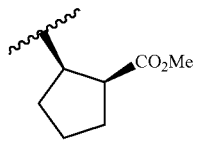 | TFA salt: 3.66–3.59(4 singlets, 3H) |

TABLE 1-continued

| Example | Ar | X | R | Selected ¹H NMR data |
|---------|-----|-----|-----|-----|
| | | | mixture of diastereomers | |
| 46 | Ph | $CH_2$ | trans-4-(CH₂—)cyclohexyl-CO₂H | TFA salt: 3.07–2.85(m, 4H), 2.23–2.17(m, 2H), 2.03–1.78(m, 7H), 1.50–1.33(m, 3H), 1.03–0.94(m, 2H) |
| 47 | Ph | $CH_2$ | trans-4-(CH₂—)cyclohexyl-CO₂Me | TFA salt: 3.64(s, 0.5H), 3.63(s, 2.5H) |
| 48 | 3,4-diF-Ph | $CH_2$ | 3,4-dichlorobenzyl | TFA salt: 7.49(d, 1H, J = 2 Hz), 7.43(d, 1H, J = 8 Hz), 7.28–7.19(m, 3H), 7.12–7.06(m, 1H), 4.46–4.27(m, 3H) |
| 49 | 3,4-diF-Ph | $CH_2$ | 4-hydroxy-3-methoxybenzyl | TFA salt: 7.28–7.05(m, 3H), 6.92–6.84(m, 1H), 6.78–6.59(m, 2H), 3.85(s, 0.6H), 3.84(s, 2.4H) |
| 50 | 3,4-diF-Ph | $CH_2$ | 4-(carboxymethoxy)-3-methoxybenzyl | TFA salt: 7.30–7.20(m, 2H), 7.12–7.07(m, 1H), 6.98–6.94(m, 1H), 6.91–6.79(m, 2H), 4.64(s, 0.3H), 4.61(s, 1.7H), 3.85(s, 3H) |
| 51 | 3,4-diF-Ph | $CH_2$ | tertButyl | TFA salt: 7.31–7.17(m, 3H), 7.17–7.05(m, 2H), 1.3(s, 9H) |
| 52 | 3,4-diF-Ph | $CH_2$ | —(CH₂)₄CO₂H | TFA salt: 7.30–7.18(m, 2H), 7.15–7.03(m, 1H), 3.27–3.13(m, 2H), 2.3–2.28(m, 2H), 1.63–1.49(m, 4H) |
| 53 | 3,4-diF-Ph | S | —(CH₂)₄CO₂H | TFA salt: 7.30–7.19(m, 2H), 7.16–7.03(m, 1H), 3.30–3.18(m, 2H), 2.36–2.28(m, 2H), 1.66–1.45(m, 4H) |

TABLE 1-continued
| Example | Ar | X | R | Selected ¹H NMR data |
|---|---|---|---|---|
| 54 | 3,4-diF-Ph | CH₂ | 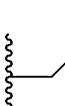 | TFA salt: 7.30–7.05(m, 7H), 4.43–4.29(m, 3H), 3.60–3.45(m, 4H) |
| 55 | 3,4-diF-Ph | S | 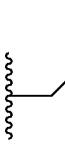 | TFA salt: 7.32–7.0(m, 7H), 4.50–4.28(m, 3H), 3.60–3.55(m, 2H) |
| 56 | 3,4-diF-Ph | CH₂ |  | TFA salt: 3.65(s, 2H), 3.60 (s, 1H) |
| 57 | 3,4-diF-Ph | CH₂ |  | TFA salt: 3.65(s, 0.6H), 3.63(s, 2.4H) |
| 58 | 3,4-diF-Ph | CH₂ | 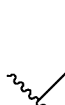 | TFA salt: 7.55(d, 0.33H, J = 8 Hz), 7.47(d, 0.67H, J = 8 Hz), 7.40–7.19(m, 4H), 7.15–6.93(m, 2H), 6.41(s, 0.33H), 6.39(s, 0.67H), 4.53–4.23(m, 3H) |
| 59 | 3,4-diF-Ph | CH₂ |  | TFA salt: 7.61–7.53(m, 1H), 7.32(d, 1H, J = 8 Hz), 7.30–6.94(m, 6H), 3.60–3.37(m, 4H), 3.02–2.80(m, 4H) |
| 60 | 3,4-diF-Ph | CH₂ | | TFA salt: 7.53–7.48(m, 2H), 7.30–7.02(m, 3H), 3.40–3.30(m, 2H), 2.80–2.67(m, 3H) |

TABLE 1-continued
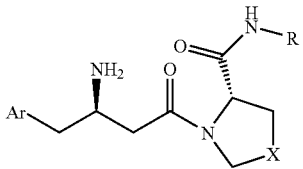
| Example | Ar | X | R | Selected ¹H NMR data |
|---|---|---|---|---|
| 61 | 3,4-diF-Ph | CH₂ | 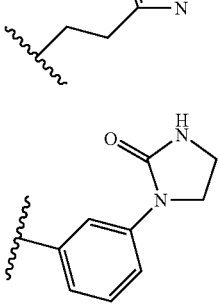 | TFA salt: 3.60–3.43(m, 4H), 3.03–2.92(m, 4H), 2.46(s, 3H) |
| 62 | 3,4-diF-Ph | CH₂ | 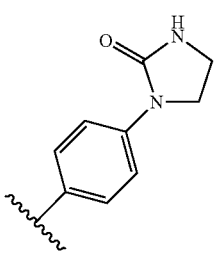 | TFA salt: 7.31–7.10(m, 6H), 7.10–6.98(m, 1H), 3.98–3.92(m, 2H), 3.60–3.48(m, 4H) |
| 63 | 3,4-diF-Ph | CH₂ | 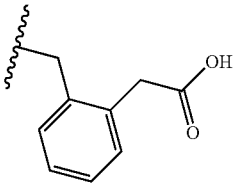 | TFA salt: 7.52–7.46(m, 4H), 7.30–6.98(m, 3H), 3.96–3.90(m, 2H), 3.60–3.48(m, 4H) |
| 64 | 3,4-diF-Ph | CH₂ | 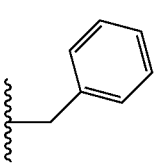 | TFA salt: 7.36–7.10(m, 6H), 7.10–7.06(m, 0.75H), 6.98–6.97(m, 0.25H), 3.81–3.70(m, 3H) |
| 65 | 2-F-Ph | CH₂ | 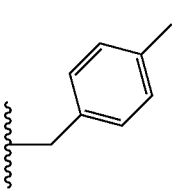 | TFA salt: 7.38–7.10(m, 9H), 4.46–4.30(m, 3H) |
| 66 | 2-F-Ph | CH₂ | 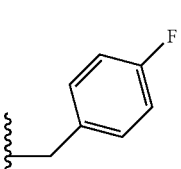 | TFA salt: 7.38–7.32(m, 2H), 7.20–7.08(m, 6H), 4.45–4.25(m, 3H), 2.31(s, 0.6H), 2.29(s, 2.4H) |
| 67 | 2-F-Ph | CH₂ |  | TFA salt: 7.38–7.25(m, 4H), 7.22–7.14(m, 2H), 7.06(t, 0.4H, J = 8Hz), 7.00(t, 1.6H, J = 8Hz), 4.43–4.29(m, 3H) |

TABLE 1-continued
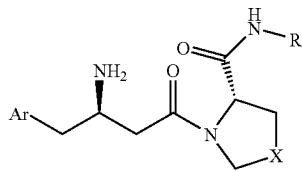
| Example | Ar | X | R | Selected $^1$H NMR data |
|---|---|---|---|---|
| 68 | 2-F-Ph | CH$_2$ | | TFA salt: 7.38–7.25(m, 6H), 7.21–7.12(m, 2H), 4.43–4.28(m, 3H) |
| 69 | 2-F-Ph | CH$_2$ | | TFA salt: 7.64(d, 0.4H, J = 8 Hz), 7.60(d, 1.6H, J = 8 Hz), 7.47(d, 2H, J = 8 Hz), 7.38–7.30(m, 2H), 7.25–7.11(m, 2H), 4.50–4.32 (m, 3H) |
| 70 | 2-F-Ph | CH$_2$ | | TFA salt: 7.52(d, 0.4H, J = 8.4 Hz), 7.44(d, 1.6H, J = 8.5 Hz), 7.38–7.33(m, 2H), 7.23–7.15(m, 4H), 4.45–4.28(m, 3H) |
| 71 | 2-F-Ph | CH$_2$ | | TFA salt: 7.36–7.12(m, 8H), 4.45–4.30(m, 3H), 3.59(s, 0.4H), 3.56(s, 1.6H) |
| 72 | 2-F-Ph | CH$_2$ | | TFA salt: 3.65–3.61(m, 3H) |
| 73 | 2-F-Ph | S | | TFA salt: 3.65(s, 2H), 3.60 (s, 1H) |

TABLE 1-continued
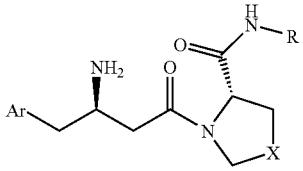
| Example | Ar | X | R | Selected $^1$H NMR data |
|---|---|---|---|---|
| 74 | 2-F-Ph | CH$_2$ | 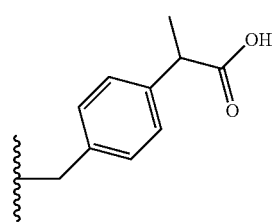<br>mixture of diastereomers | TFA salt: 2.92–2.85(m, 0.5H), 2.62–2.55(1.5H), 1.41(d, 3H, J '2 7 Hz) |
| 75 | 2-F-Ph | CH$_2$ | 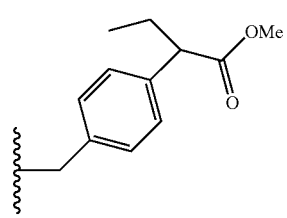<br>mixture of diastereomers | TFA salt: 3.62–3.55(m, 3H), 3.54–3.42(m, 3H), 0.85(t, 3H, J = 7.4 Hz) |
| 76 | 2-F-Ph | CH$_2$ | 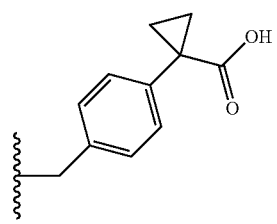 | TFA salt: 1.60–1.48(m, 2H), 1.18–1.06(m, 2H) |
| 77 | 2-F-Ph | CH$_2$ | 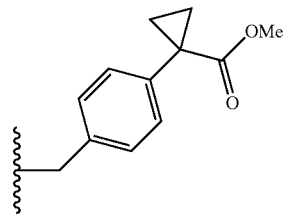 | TFA salt: 3.57(s, 2.5H), 3.56(s, 0.5H), 1.58–1.53 (m, 2H), 1.18–1.13(m, 2H) |
| 78 | 2-F-Ph | CH$_2$ | 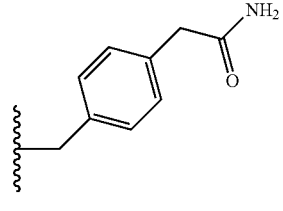 | TFA salt: 7.38–7.12(m, 8H), 4.45–4.25(m, 3H), 3.60–3.39(m, 4H) |

TABLE 1-continued
| Example | Ar | X | R | Selected ¹H NMR data |
|---|---|---|---|---|
| 79 | 2-F-Ph | CH$_2$ |  | TFA salt: 2.65–2.56(m, 2H), 0.72–0.65(m, 2H), 0.47–0.41(m, 2H) |
| 80 | 2-F-Ph | CH$_2$ |  | TFA salt: 3.18(q, 2H, J = 7 Hz), 1.06(t, 3H, J '2 7 Hz). |
| 81 | 2-F-Ph | CH$_2$ |  | TFA salt: 7.39–7.10(13H), 3.60–3.40(m, 4H) |
| 82 | 2-F-Ph | CH$_2$ |  | TFA salt: 3.06(s, 0.55H), 3.03(s, 2.45H), 2.93(s, 2.45H), 2.91(s, 0.55H) |
| 83 | 2-F-Ph | CH$_2$ |  | TFA salt: 3.61–3.40(m, 8H) |

TABLE 1-continued

| Example | Ar | X | R | Selected ¹H NMR data |
|---|---|---|---|---|
| 84 | 2-F-Ph | CH$_2$ | 4-sulfamoylbenzyl (-CH$_2$-C$_6$H$_4$-SO$_2$NH$_2$) | TFA salt: 7.89(d, 0.4H, J = 8.5 Hz), 7.83(d, 1.6H, J = 8.5 Hz), 7.45(d, 2H, J = 8.3 Hz), 7.38–7.31(m, 2H), 7.24–7.12(m, 2H), 4.50–4.32(m, 3H) |
| 85 | 2-F-Ph | CH$_2$ | 4-(1,2,3-thiadiazol-5-yl)benzyl | TFA salt: 9.21(s, 0.2H), 9.19(s, 0.8H), 8.10(s, 0.4H, J '2 8 Hz), 8.04(d, 1.6H, J '2 8.2 Hz), 7.45(d, 2H, J '2 8.2 Hz), 7.37–7.30(m, 2H), 7.20–7.09(m, 2H), 4.50–4.32(m, 3H) |
| 86 | 2-F-Ph | CH$_2$ | 4-(1H-imidazol-4-yl)benzyl | TFA salt: 8.97(s, 1H), 7.86(s, 1H)(, 7.73(d, 0.4H, J '2 8.2 Hz), 7.68(d, 1.6H, J '2 8.2Hz), 7.47–7.42(m, 2H), 7.38–7.32(m, 2H), 7.21–7.11(m, 2H), 4.50–4.35(m, 3H) |
| 87 | 2-F-Ph | CH$_2$ | 3-(1H-pyrazol-1-yl)benzyl | TFA salt: 8.27(s, 1H), 7.74–7.60(m, 3H), 7.50–7.39(m, 1H), 7.38–7.22(m, 3H), 7.19–7.05(m, 2H), 6.52(s, 1H), 4.53–4.34(m, 3H) |
| 88 | 2-F-Ph | CH$_2$ | 3-(1H-imidazol-5-yl)benzyl | Bis TFA salt: 8.97(s, 1H), 7.96(s, 1H), 7.70–7.63(m, 1H), 7.60(d, 1H, J = 7 Hz), 7.53–7.38(m, 2H), 7.18–7.08(m, 2H), 4.45–4.30(m, 3H) |
| 89 | 2-F-Ph | CH$_2$ | 4-((1H-imidazol-4-yl)methyl)benzyl | Bis TFA salt: 8.77(s, 1H), 7.38–7.09(m, 9H), 4.50–4.35(m, 3H), 4.07–4.02(m, 2H) |

TABLE 1-continued
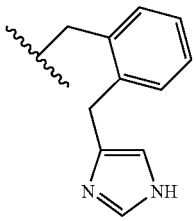
| Example | Ar | X | R | Selected $^1$H NMR data |
|---|---|---|---|---|
| 90 | 2-F-Ph | CH$_2$ | 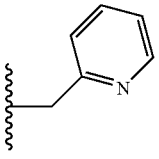 | Bis TFA salt: 8.78(s, 1H), 7.38–7.09(m, 9H), 4.45–4.33(m, 3H), 4.19–4.10(m, 2H) |
| 91 | 2-F-Ph | CH$_2$ | 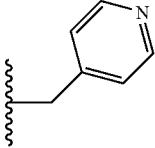 | Bis TFA salt: 8.72–8.60(m, 1H), 8.40(t, 1H, J = 8 Hz), 7.94(d, 1H, J = 8 Hz), 7.85–7.69(m, 1H), 7.38–7.28(m, 2H), 7.20–7.11(m, 2H), 4.77–4.61(m, 2H) |
| 92 | 2-F-Ph | CH$_2$ | 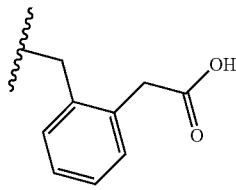 | Bis TFA salt: 8.72(bs, 2H), 7.92(bs, 2H), 7.38–7.28 (m, 2H), 7.20–7.11(m, 2H), 4.70–4.53(m, 2H) |
| 93 | 2-F-Ph | CH$_2$ | 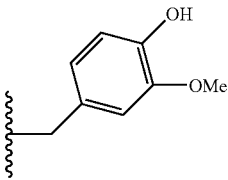 | TFA salt: 7.38–7.10(m, 8H), 4.45–4.39(m, 3H), 3.76(s, 0.4H), 3.71(s, 1.8H) |
| 94 | 2-F-Ph | CH$_2$ | 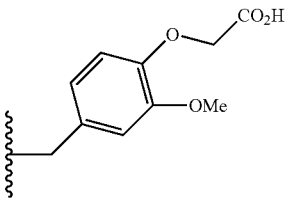 | TFA salt: 7.38–7.32(m, 2H), 7.22–7.10(m, 2H), 6.88(d, 0.15H, J '2 1.6Hz), 6.86(d, 0.85H), J = 1.1 Hz), 6.78–6.67(m, 2H), 3.85(s, 0.5H), 3.83(s, 2.5H) |
| 95 | 2-F-Ph | CH$_2$ | 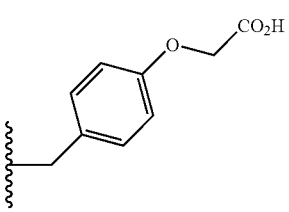 | TFA salt: 7.38–7.31(m, 2H), 7.22–7.11(m, 2H), 6.94–6.92(m, 1H), 6.90–6.78(m, 2H), 4.63(s, 0.3H), 4.61(s, 1.7H), 3.85 (s, 0.45H), 3.84(s, 2.55H) |
| 96 | 2-F-Ph | CH$_2$ |  | TFA salt: 7.38–7.31(m, 2H), 7.25–7.06(m, 4H), 6.91(d, 0.35H, J = 8.6 Hz), 6.86(d, 1.65H, J = 8.7 Hz), 4.64(s, 0.35H), 4.61(s, 1.65H), 4.43–4.25(m, 3H) |

TABLE 1-continued

| Example | Ar | X | R | Selected ¹H NMR data |
|---|---|---|---|---|
| 97 | 2-F-Ph | $CH_2$ | 4-(1-carboxyethoxy)benzyl (mixture of diastereomers) | TFA salt: 7.38–7.31(m, 2H), 7.23–7.08(m, 4H), 6.88(d, 0.33H, J = 8.5 Hz), 6.82(d, 1.67H, J = 8.7 Hz), 4.80–4.73(m, 1H), 4.42–4.25(m, 3H), 1.56(d, 3H, J = 6.9 Hz) |
| 98 | 2-F-Ph | $CH_2$ | 4-(2-carboxypropan-2-yloxy)benzyl | TFA salt: 7.38–7.32(m, 2H), 7.21–7.10(m, 4H), 6.88(d, 0.36H, J = 8.5 Hz), 6.83(d, 1.64H, J = 8.5 Hz), 4.45–4.25(m, 3H), 1.54(s, 0.54H), 1.53(s, 2.46H) |
| 99 | 2-F-Ph | $CH_2$ | 4-(1-carboxypropoxy)benzyl (mixture of diastereomers) | TFA salt: 7.38–7.32(m, 2H), 7.24–7.10(m, 4H), 6.88(d, 0.32H, J = 8.2 Hz), 6.83(s, 1.68H, J = 8.4 Hz), 4.62–4.55(m, 1H), 4.42–4.21(m, 3H), 2.05–1.83(m, 5H), 1.09–1.00(m, 3H) |
| 100 | 2-F-Ph | $CH_2$ | 4-(1-ethoxycarbonylpropoxy)benzyl (mixture of diastereomers) | TFA salt: 4.20–4.13(m, 2H), 1.25–1.20(m, 3H) |
| 101 | 2-F-Ph | S | 4-(1-carboxypropoxy)benzyl | TFA salt: 7.38–7.32(m, 2H), 7.26–7.11(m, 4H), 6.90–6.79(m, 2H), 2.02–1.90(m, 2H), 1.06(t, 3H, J = 7 Hz) |

TABLE 1-continued
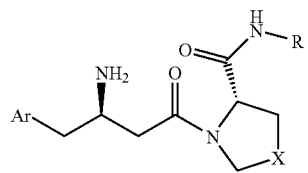
| Example | Ar | X | R | Selected ¹H NMR data |
|---|---|---|---|---|
| | | | isomer 1 | |
| 102 | 2-F-Ph | S | (4-CH₂-phenoxy)-CH(Et)-CO₂Et | TFA salt: 4.21–4.13(m, 2H), 1.25–1.20(m, 3H) |
| | | | isomer 1 | |
| 103 | 2-F-Ph | S | (4-CH₂-phenoxy)-CH(Et)-CO₂H | TFA salt: 7.38–7.32(m, 2H), 7.26–7.10(m, 4H), 6.89–6.80(m, 2H), 2.01–1.90(m, 2H), 1.07(t, 3H), H = 7 Hz) |
| | | | isomer 2 | |
| 104 | 2-F-Ph | S | (4-CH₂-phenoxy)-CH(Et)-CO₂Et | TFA salt: 4.21–4.15(m, 2H), 1.23(t, 3H, J '2 7.1 Hz) |
| | | | isomer 2 | |
| 105 | 2-F-Ph | CH₂ | (4-CH₂-phenoxy)-CH(Pr)-CO₂H | TFA salt: 4.66–4.60(m, 1H), 2.03–1.94(m, 5H), 1.59–1.48(m, 2H), 0.98(t, 3H, J = 7.5 Hz) |
| | | | mixture of diastereomers | |
| 106 | 2-F-Ph | CH₂ | (4-CH₂-phenoxy)-CH(Pr)-CO₂Et | TFA salt: 4.20–4.13(m, 2H), 1.22–1.19(m, 3H) |

TABLE 1-continued
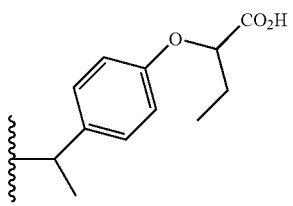
| Example | Ar | X | R | Selected $^1$H NMR data |
|---|---|---|---|---|
| | | | mixture of diastereomers | |
| 107 | 2-F-Ph | CH$_2$ | 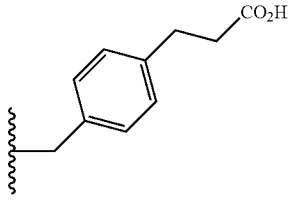<br>mixture of diastereomers | TFA salt: 5.00–4.90(m, 1H), 4.63–4.55(m, 1H), 2.10–1.78(m, 5H), 1.44–1.39(m, 3h), 1.06(td, 3H, J = 7.6, 1.5 Hz) |
| 108 | 2-F-Ph | CH$_2$ | 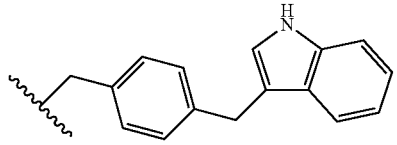 | TFA salt: 2.91–2.83 (m, 2H), 2.63–2.54(m, 3H) |
| 109 | 2-F-Ph | CH$_2$ | 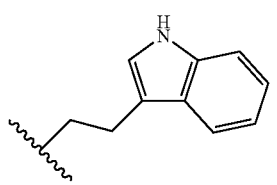 | TFA salt: 7.37–7.22(m, 4H), 7.20–6.97(m, 8H), 6.91–6.85(m, 1H), 4.43–4.20(m, 3H), 4.07(s, 0.4H), 4.05(s, 1.6H) |
| 110 | 2-F-Ph | CH$_2$ | 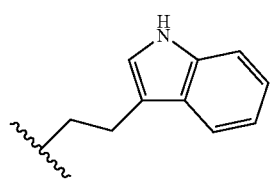 | TFA salt: 7.57(d, 0.2H, J = 8 Hz), 7.54(d, 0.8H, J = 8 Hz), 7.38–7.25(m, 3H), 7.22–6.93(m, 5H), 3.60–3.35(m, 4H), 2.98–2.90(m, 2H) |
| 111 | 2-F-Ph | S | 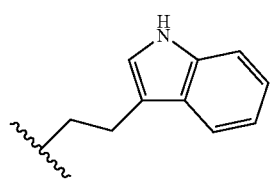 | TFA salt: 7.59–7.56(m, 1H), 7.39–7.26(m, 3H), 7.30–7.03(m, 4H), 7.02–6.87(m, 1H), 3.50–3.43(m, 2H), 3.13–2.90(m, 4H) |
| 112 | 2-F-Ph | CH$_2$ | 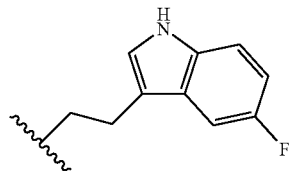 | TFA salt: 7.54–7.46(m, 1H), 7.37–7.26(m, 2H), 7.24–7.07(m, 2H), 7.06–6.99(m, 2H), 6.82–6.75(m, 1H), 3.50–3.33(m, 4H), 2.95–2.87(m, 2H) |

TABLE 1-continued

| Example | Ar | X | R | Selected ¹H NMR data |
|---|---|---|---|---|
| 113 | 2-F-Ph | CH$_2$ | (2-methyl-1H-indol-3-yl)propyl | TFA salt: 7.47–7.41(m, 1H), 7.38–7.09(m, 5H), 7.01–6.88(m, 2H), 3.53–3.30(m, 4H), 2. 2.87(t, 2H, J = 7.6 Hz), 2.38(s, 0.6 H), 2.37(s, 2.4) |
| 114 | 2-F-Ph | CH$_2$ | (5-cyano-2-methyl-1H-indol-3-yl)propyl | TFA salt: 7.98–7.86(m, 1H), 7.38–7.25(m, 4H), 7.22–7.09(m, 2H), 3.60–3.25(m, 4H), 2.93–2.85(m, 2H), 2.41–2.37(m, 3H) |
| 115 | 2-F-Ph | CH$_2$ | (1H-indol-3-yl)butyl | TFA salt: 7.54–7.48(m, 1H), 7.37–7.25(m, 3H), 7.23–6.93(m, 5H), 3.29–3.19(m, 2H), 2.82–2.73(m, 3H), 2.20–1.80(m, 5H) |
| 116 | 2-F-Ph | CH$_2$ | (1H-imidazol-4-yl)propyl | Bis TFA salt: 8.79(s, 1H), 7.39–7.26(m, 3H), 7.21–7.12(m, 2H), 3.56–3.38(m, 4H), 2.93–2.85(m, 2H) |
| 117 | 2-F-Ph | CH$_2$ | (1H-imidazol-4-yl)butyl | Bis TFA salt: 8.79–8.73(m, 1H), 7.38–7.26(m, 3H), 7.21–7.09(m, 2H), 3.3–3.15 (m, 2H), 2.80–2.69(m, 2H), 1.80–1.65(m, 3H), 1.59–1.50(m, 2H) |
| 118 | 2-F-Ph | CH$_2$ | (2H-tetrazol-5-yl)butyl | TFA salt: 3.30–3.11(m, 2H), 2.96(t, 2H, J = 7.6 Hz), 1.89–1.77(m, 2H), 1.61–1.51(m, 2H) |
| 119 | 2-F-Ph | CH$_2$ | (4-hydroxyphenyl)propyl | TFA salt: 7.39–7.22(m, 2H), 7.21–7.12(m, 2H), 7.02–6.98(m, 2H), 6.72–6.68(m, 2H), 3.58–3.30(m, 4H), 2.88–2.63(m, 3H) |

TABLE 1-continued
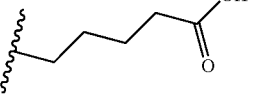
| Example | Ar | X | R | Selected $^1$H NMR data |
|---|---|---|---|---|
| 120 | 2-F-Ph | CH$_2$ | 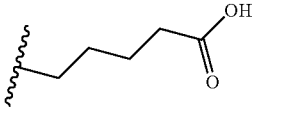 | TFA salt: 7.39–7.28(m, 2H), 7.21–7.11(m, 2H), 3.22–3.15(m, 2H), 2.34(t, 0.6H, J '2 8 Hz), 2.29(t, 1.4H, J = 8 Hz), 1.63–1.49 (m, 4H) |
| 121 | 2-F-Ph | S | 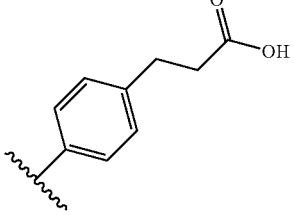 | TFA salt: 3.27–2.96(m, 5H), 2.35–2.26(m, 2H), 1.65–1.43(m, 4H) |
| 122 | 2-F-Ph | S | 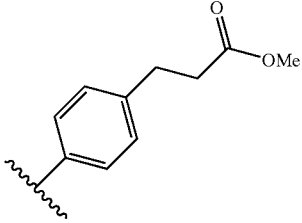 | TFA salt: 7.47(d, 2H, J '2 8.4 Hz), 7.43(d, 2H, J '2 8.5 Hz), 7.30–7.12(m, 4H), 2.94–2.85(m, 3H), 2.62–2.54(m, 2H) |
| 123 | 2-F-Ph | S | 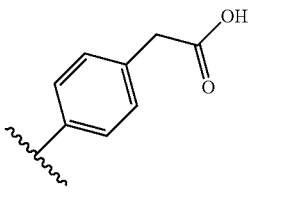 | TFA salt: 3.62(s, 3H) |
| 124 | 2-F-Ph | CH$_2$ | 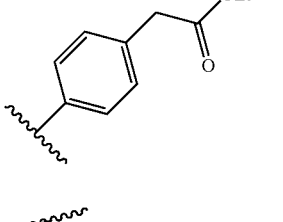 | TFA salt: 7.55–7.48(m, 2H), 7.38–7.33(m, 2H), 7.28–6.97(m, 4H), 3.62–3.43(m, 4H), |
| 125 | 2-F-Ph | CH$_2$ | 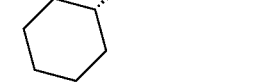 | TFA salt: 4.16–4.08(m, 2H), 1.21(t, 3H, J = 7.1 Hz) |
| 126 | 2-F-Ph | CH$_2$ |  | TFA salt: 7.38–7.25(m, 2H), 7.20–7.10(m, 2H), 3.95–3.79(m, 2H), 2.40–2.20(m, 1H), 2.00–1.70(m, 7H), 1.58–1.45(m, 1H), 1.42–1.20(m, 3H) |

TABLE 1-continued

| Example | Ar | X | R | Selected ¹H NMR data |
|---|---|---|---|---|
| | | | mixture of diastereomers | |
| 127 | 2-F-Ph | S | cyclohexyl-CO₂H | TFA salt: 7.40–7.25(m, 2H), 7.21–7.12(m, 2H), 3.98–3.91(m, 2H), 2.43–2.25(m, 1H), 2.02–1.70(m, 4H), 1.59–1.43(m, 1H), 1.42–1.20(m, 3H) |
| | | | mixture of diastereomers | |
| 128 | 2-F-Ph | CH₂ | cyclohexyl-CO₂Et | TFA salt: 7.38–7.28(m, 2H), 7.20–7.10(m, 2H), 4.12–4.00(m, 2H), 3.95–3.87(m, 1H), 2.40–2.20(m, 1H), 2.00–1.70(m, 7H), 1.57–1.45(m, 1H), 1.42–1.18(m, 6H) |
| | | | mixture of diastereomers | |
| 129 | 2-F-Ph | S | cyclohexyl-CO₂Et | TFA salt: 7.40–7.25(m, 2H), 7.21–7.10(m, 2H), 4.18–4.00(m, 2H), 3.99–3.81(m, 2H), 2.53–2.30(m, 1H), 1.98–1.69(m, 4H), 1.59–1.42(m, 1H), 1.42–1.18(m, 6H) |
| | | | mixture of diastereomers | |
| 130 | 2-F-Ph | CH₂ | cyclohexyl-CO₂H | TFA salt: 7.39–7.26(m, 2H), 7.21–7.10(m, 2H), 4.30–4.10(m, 1H), 2.79–2.69(m, 2H), 2.18–1.78(m, 6H), 1.72–1.38(m, 6H) |
| | | | mixture of diastereomers | |
| 131 | 2-F-Ph | S | cyclohexyl-CO₂H | TFA salt: 7.40–7.25(m, 2H), 7.22–7.10(m, 2H), 4.28–4.07(m, 1H), 2.80–2.67(m, 2H), 2.03–1.37(m, 8H) |
| | | | mixture of diastereomers | |
| 132 | 2-F-Ph | CH₂ | cyclohexyl-CO₂Et | TFA salt: 7.39–7.26(m, 2H), 7.21–7.11(m, 2H), 4.34–4.19(m, 1H), 4.12–3.98(m, 2H), 2.79–2.70(m, 2H), 2.04–1.78(m, 5H), 1.62–1.38(m, 6H), 1.30–1.18(m, 3H) |

TABLE 1-continued
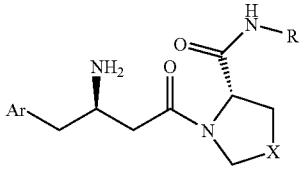
| Example | Ar | X | R | Selected ¹H NMR data |
|---|---|---|---|---|
mixture of diastereomers
| 133 | 2-F-Ph | S | 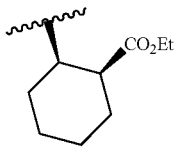 | TFA salt: 7.40–7.25(m, 2H), 7.21–7.10(m, 2H), 4.32–4.18(m, 1H), 4.18–3.99(m, 2H), 2.90–2.70(m, 3H), 1.99–1.37(m, 8H), 1.30–1.17(m, 3H) |
mixture of diastereomers
| 134 | 2-F-Ph | CH₂ | 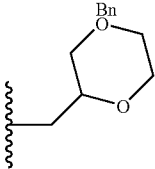 | TFA salt: 7.53–7.45(m, 5H), 7.37–7.25(m, 2H), 7.20–7.08(m, 2H), 4.39–4.26(m, 3H), 4.16–4.-1 (m, 1H) 3.87–3.73(m, 3H), 3.55–3.24(m, 6H), 3.19–2.94(m, 4H) |
mixture of diastereomers
| 135 | 2-MePh | CH₂ | 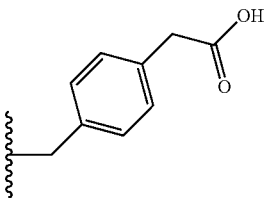 | TFA salt: 2.36(s, 2.5H), 2.31(s, 0.5H) |
| 136 | 2-MePh | CH₂ | 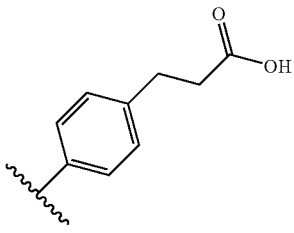 | TFA salt: 7.48(d, 0.5H, J = 8.5 Hz), 7.43(d, 1.5H, J = 8.5 Hz), 7.23–7.09(m, 6H), 2.93–2.85(m, 2H), 2.62–2.54(m, 3H), 2.36(s, 2.25H), 2.28(s, 0.75H) |
| 137 | 2-MePh | CH₂ | 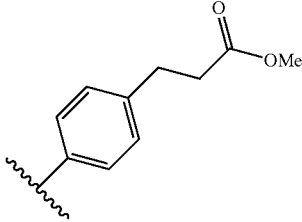 | TFA salt: 3.63(s, 0.6H), 3.62(s, 2.4H) |

TABLE 2

| Example | Ar | X | R' | Selected $^1$H NMR data |
|---|---|---|---|---|
| 138 | 2-F-Ph | CH$_2$ | (3-(MeNH-CH$_2$)-phenyl) | TFA salt: 7.40–7.10(m, 9H), 4.70–4.51(m, 2H), 3.05(s, 2H), 2.87(s, 1H) |

Example 139

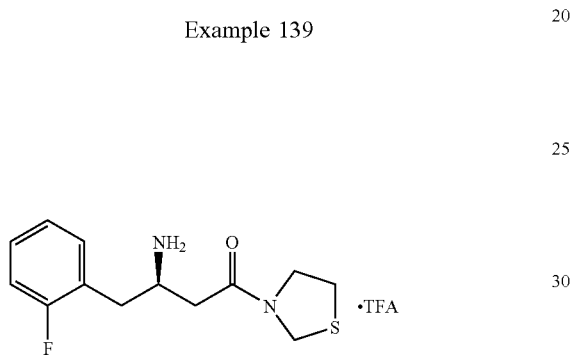

(2R)-1-(2-Fluorophenyl)-4-oxo-4-(1,3-thiazolidin-3-yl)butan-2-amine, trifluoroacetate salt. To a solution of 56 mg (0.188 mmol) of (3R)-3-[(tert-butoxycarbonyl)amino]-4-(2-fluorophenyl)butanoic acid in 1 mL of DMF was added 0.0445 mL (0.56 mmol) of thiazolidine, 54.2 mg (0.28 mmol) of 1-ethyl-3-(3-dimethylaminopropyl)carbodiimide hydrochloride (EDC), 38.2 mg (0.28 mmol) of 1-hydroxybenzotriazole hydrate (HOBT), and 0.0656 mL (0.38 mmol) of diisopropylethylamine (DIEA). The mixture was stirred for 16 h and diluted with ethyl acetate. The organic phase was washed sequentially with 1N hydrochloric acid and 1N aqueous sodium hydroxide solution, and concentrated in vacuo. The residue was purified by preparative TLC (silica gel, 1:1 ethyl acetate) to give 72 mg of amide. This material was dissolved in 2 mL of methylene chloride and 2 mL trifluoroacetic acid was added. The solution was stirred at ambient temperature for 2 h, the solvent removed in vacuo and the residual oil dissolved in methylene chloride and concentrated to remove excess trifluoroacetic acid to give the desired product. $^1$H NMR (500 MHz, CD$_3$OD) δ 7.35 (m, 2H), 7.31 (m, 2H), 4.52 (m, 2H), 3.89 (m, 1H), 3.78 (m, 1H), 3.62 (m, 1H), 3.15 (m, 4H), 2.89 (m, 4H), 2.62 (m, 1H).

Following the procedure outlined for Example 139, the compounds listed in Table 3 were prepared as their trifluoracetate salts.

TABLE 3

| Example | R | Selected $^1$H NMR data (trifluoroacetate salt) |
|---|---|---|
| 140 | Ph | 7.28(m, 2H), 7.20(m, 3H) |
| 141 | 4-Cl-Ph | 7.26(md, J = 7.5 Hz, 2H), 7.15(d, J = 7.5 Hz, 2H) |
| 142 | 3,4-diCl-Ph | 7.39(m, 2H), 7.14(d, J = 8.0 Hz, 1H) |
| 143 | 3,4-diF-Ph | 7.26(m, 2H), 7.08(m, 1H) |
| 144 | 2,3-diF-Ph | 7.18(m, 3H) |
| 145 | 2,4-diF-Ph | 7.38(m, 1H), 6.98(m, 2H) |
| 146 | 2,5-diF-Ph | 7.13(m, 2H), 7.05(m, 1H) |
| 147 | 3-benzothiophene | 7.90(m, 2H), 7.35(m, 3H) |
| 148 | 4-I-Ph | 7.60(d, J = 8.0 Hz, 2H), 7.00(d, J = 8.0 Hz, 2H) |
| 149 | 3-F-Ph | 7.26(m, 1H), 7.02(d, J '2 7.5 Hz), 6.95(m, 2H) |
| 150 | 4-F-Ph | 7.29(m, 2H), 7.07(m, 2H) |
| 151 | 2-naphthyl | 7.76(m, 3H), 7.40(m, 4H) |
| 152 | 1-naphthyl | 7.84(m, 2H), 7.72(m, 1H), 7.51(m, 2H), 7.35(m, 2H) |
| 153 | 2-CF$_3$-Ph | 7.62(m, 1H), 7.50(m, 2H), 7.38(m, 1H) |
| 154 | 3-CF$_3$-Ph | 7.48(m, 4H) |
| 155 | 4-CF$_3$-Ph | 7.55(d, J = 8.0 Hz, 2H), 7.40(d, J = 8.0 Hz, 2H) |
| 156 | 2-CN-Ph | 7.66(m, 1H), 7.58(m, 1H), 7.45(m, 1H), 7.38(m, 1H) |
| 157 | 3-CN-Ph | 7.55(m, 3H), 7.46(m, 1H) |
| 158 | 4-CN-Ph | 7.63(d, J = 8.0 Hz, 2H), 7.41(d, J = 8.0 Hz, 2H) |
| 159 | 2-Me-Ph | 7.21–7.15(m, 4H), 2.32(s, 3H) |

Example 160

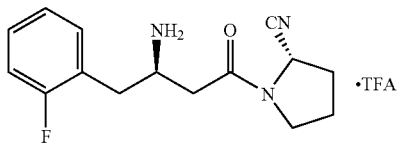

(2S)-1-[(3R)-3-Amino-4-(2-fluorophenyl)butanoyl]pyrrolidine-2-carbonitrile, trifluoroacetate salt. To a solution of 228 mg (0.77 mmol) of (3R)-3-[(tert-butoxycarbonyl)amino]-4-(2-fluorophenyl)butanoic acid in 1 mL of DMF was added 175 mg (1.54 mmol) of L-prolinamide, 176.4 mg (0.92 mmol) of 1-ethyl-3-(3-dimethylaminopropyl)carbodiimide hydrochloride (EDC), 124 mg (0.92 mmol) of 1-hydroxybenzotriazole hydrate (HOBT), and 0.267 mL (1.54 mmol) of diisopropylethylamine (DIEA). The mixture was stirred for 72 h and diluted with ethyl acetate. The organic phase was washed sequentially with 1N hydrochloric acid and 1N aqueous sodium hydroxide solution, and concentrated in vacuo. The residue was purified by preparative TLC (silica gel, 1:1 hexanes:ethyl acetate) to give 170 mg of coupled product. This material was dissolved in 5 mL of N,N-dimethylformamide and 137 mg (0.742 mmol) of cyanuric chloride was added. The resulting mixture was stirred for 3 h at ambient temperature, diluted with ethyl acetate, and quenched with saturated aqueous sodium bicarbonate solution. The organic layer was separated, concentrated in vacuo, and the residue purified by preparative thin layer chromatography (silica gel, 1:2, hexane: ethyl acetate) to give 170 mg of product. This material was dissolved in 2 mL of methylene chloride and 2 mL trifluoroacetic acid was added. The solution was stirred at ambient temperature for 2 h, the solvent removed in vacuo and the residual oil dissolved in methylene chloride and concentrated to remove excess trifluoroacetic acid to give the title compound. $^1$H NMR (500 MHz, CD$_3$OD) δ. 7.38–7.30 (m, 2H), 7.21–7.13 (m, 2H), 3.93–3.80 (m, 1H), 3.61–3.52 (m, 1H), 3.42–3.35 (m, 1H), 3.17–3.03 (m, 3H), 2.88–2.55 (m, 2H), 2.33–2.10 (m, 4H).

Example 161

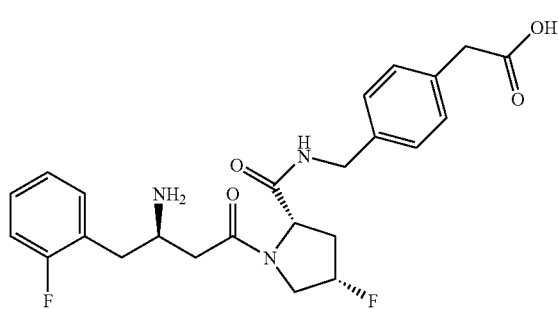

Step A. tert-Butyl [4-({[(4S)-1-(tert-butoxycarbonyl)-4-fluoro-L-prolyl]amino}methyl)phenyl]acetate. 1-Ethyl-3-(3-dimethylaminopropyl)carbodiimide hydrochloride (68 mg, 0.35 mmol) was added to a stirred solution of (4S)-1-(tert-butoxycarbonyl)-4-fluoro-L-proline (75 mg, 0.32 mmol; prepared as described by L. Demange, et al., Tetrahedron Lett., 1998, 39, 1169–1172) and 1-hydroxybenzotriazole (54 mg, 0.40 mmol) in THF (5.0 mL). After 35 min., a suspension containing the oxalate salt of tert-butyl [4-(aminomethyl)phenyl]acetate (109 mg, 0.35 mmol) and N,N-diisopropylethylamine (0.061 mL, 45 mg, 0.35 mmol) in THF (2.0 mL) was added with the aid of additional THF (2×0.5 mL), and the resultant mixture was stirred overnight at ambient temperature. The mixture was then diluted into ethyl acetate (50 mL), and washed sequentially with 2 N hydrochloric acid (20 mL), saturated aqueous sodium bicarbonate (10 mL), and saturated aqueous sodium chloride (10 mL). The organic layer was dried (sodium sulfate), decanted, and evaporated. The crude product was purified by flash column chromatography on silica gel (15% ethyl acetate in methylene chloride) to give 111 mg of the title compound as a colorless syrup which crystallized upon standing. $^1$H NMR (500 MHz, CD$_3$OD) δ 7.26 (d, 2H, J=6 Hz), 7.19 (d, 2H, J=6 Hz), 5.23 (dt, 1H, J=52, 3 Hz), 4.53–4.21 (m, 3H), 3.76 (dd, 1H, J=24, 13 Hz), 3.64 (ddd, J=36, 13, 3), 3.49 (s, 2H), 2.58–2.32 (m, 2H), 1.48 (s, 3H), 1.41 (s, 9H), 1.37 (s, 6H).

Step B. tert-Butyl [4-({[(4S)-4-fluoro-L-prolyl]amino}methyl)phenyl]acetate. Methanesulfonic acid (0.030 mL, 44 mg, 0.46 mmol) was added to a stirred solution of tert-butyl [4-({[(4S)-1-(tert-butoxycarbonyl)4-fluoro-L-prolyl]amino}methyl)phenyl]acetate (97 mg, 0.22 mmol) in a mixture of tert-butyl acetate (1.0 mL) and methylene chloride (0.25 mL), following a general procedure described by L. S. Lin, et al. (Tetrahedron Lett., 2000, 41, 7013–7016). After 6 h, the mixture was added to saturated aqueous sodium bicarbonate (15 mL) and extracted with ethyl acetate (30 mL). The organic layer was washed with saturated aqueous sodium chloride (10 mL), dried (sodium sulfate), decanted and evaporated. The crude product was purified by flash column chromatography on silica gel (3% methanol/0.6% conc. ammonium hydroxide/methylene chloride) to give 29 mg of the title compound. $^1$H NMR (500 MHz, CD$_3$OD) δ 7.23 (d, 2H, J=8 Hz), 7.20 (d, 2H, J=8 Hz), 5.18 (dt, 1H, J=52, 4 Hz), 4.41 (d, 1H, J=14 Hz), 4.35 (d, 1H, J=14 Hz), 3.76 (dd, 1H, J=10, 3 Hz), 3.50 (s, 2H), 3.25 (dd, J=22, 14 Hz), 3.05 (ddd, 1H, J=36, 14, 4 Hz), 2.33 (dddd, 1H, J=40, 14, 10, 4 Hz), 2.22 (ddm, 1H, J=24, 14 Hz).

Step C. tert-Butyl {4-[({(4S)-1-[(3R)-3-[(tert-butoxycarbonyl)amino]-4-(2-fluorophenyl)butanoyl]-4-fluoro-L-proly}amino)methyl]phenyl}acetate. 1-Hydroxybenzotriazole (14 mg, 0.10 mmol) and 1-ethyl-3-(3-dimethylaminopropyl)carbodiimide hydrochloride (20 mg, 0.10 mmol) were added to a solution of (3R)-3-[(tert-butoxycarbonyl)amino]-4-(2-fluorophenyl)butanoic acid (28 mg, 0.094 mmol) and tert-butyl [4-({[(4S)-4-fluoro-L-prolyl]amino}methyl)phenyl]acetate (29 mg, 0.086 mmol) in DMF (1.0 mL). The mixture was stirred overnight at ambient temperature, then diluted into ethyl acetate (35 mL) and washed sequentially with 2 N hydrochloric acid, saturated aqueous sodium bicarbonate, and saturated aqueous sodium chloride (10 mL each). The organic layer was dried (sodium sulfate), decanted, and evaporated. The crude product was purified by flash column chromatography on silica gel (50% ethyl acetate in methylene chloride) to give 51 mg of the title compound as a colorless brittle glass. $^1$H NMR (500 MHz, CD$_3$OD) δ 7.30–6.98 (m, 8H), 5.30 (d, 0.75H, J=52 Hz), 5.24 (d, 0.25H, J=52 Hz), 3.49 (s, 0.5H), 3.46 (s, 1.5H), 1.40 (s, 9H), 1.34 (s, 2.2H), 1.32 (s, 6.8H).

Step D. {4-[({(4S)-1-[(3R)-3-Amino-4-(2-fluorophenyl)butanoyl]-4-fluoro-L -prolyl}amino)methyl]phenyl}acetic acid. Trifluoroacetic acid (2.0 mL) was added to a stirred solution of tert-butyl {4-[({(4S)-1-[(3R)-3-[(tert-butoxycarbonyl)amino]-4-(2-fluorophenyl)butanoyl]-4-fluoro-L-prolyl}amino)methyl]phenyl}acetate (50 mg, 0.081 mmol) in methylene chloride (2.0 mL) at ambient temperature. After 4 h, the solution was concentrated under vacuum. Additional methylene chloride (2×5 mL) was added, with evaporation after each addition. The residue was loaded onto a Varian Mega Bond Elut SCX column in methanol. The product, which eluted from the column with 2 M ammonia in methanol, was recrystallized from boiling acetonitrile to give 20 mg of the title compound as fine white crystals. $^1$H NMR (500 MH, CD$_3$OD) δ 7.39 (m, 8H), 5.28 (d, 0.6H, J=52 Hz), 5.22 (d, 0.4H, J=52 Hz), 4.65–4.59 (m, 0.6H), 4.44–4.26 (m, 2.4H), 3.88–3.57 (m, 3H), 3.47 (s, 0.8H), 3.44 (s, 1.2H), 3.08–2.94 (m, 1.6H), 2.84 (dd, 0.4H, J=14, 8 Hz), 2.74 (dd, 0.6H, J=17, 3 Hz), 2.68–2.31 (m, 3H), 2.18 (dd, 0.4H, J=17, 9 Hz).

Example 162

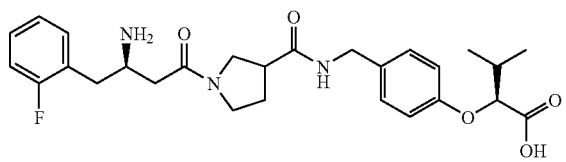

Step A. Benzyl 1-[(3R)-3-[(tert-butoxycarbonyl)amino]-4-(2-fluorophenyl)butanoyl]pyrrolidine-3-carboxylate. To a solution of 200 mg (0.67 mmol) of (3R)-3-[(tert-butoxycarbonyl)amino]-4-(2-fluorophenyl)butanoic acid and 179 mg (0.74 mmol) of the hydrochloride salt of (RS)-pyrrolidine-3-carboxylic acid benzyl ester in 5 mL of tetrahydrofuran was added 153 mg (0.8 mmol) of 1-ethyl-3-(3-dimethylaminopropyl)carbodiimide hydrochloride (EDC) and 0.1 mL (0.74 mmol) of triethylamine (TEA). The mixture was stirred for 16 h and then submitted directly to Biotage chromatography (silica gel, 60–70% ethyl acetate in hexanes) to give 0.290 g of the coupled product. MS: 385.1 (M+H). $^1$H NMR (500 MHz, CD$_3$OD) δ 7.38(m, 5H), 7.22(m, 2H), 7.09(m, 2H), 5.88(m, 1H), 5.24(m, 2H), 4.61 (m, 1H), 4.20(m, 1H), 3.50(m, 1H), 3.31(m, 1H), 3.01(m, 2H), 2.52(m, 2H), 2.20(m, 1H), 2.02(m, 3H), 1.40(s, 9H).

Step B. 1-[(3R)-3-[(tert-butoxycarbonyl)amino]-4-(2-fluorophenyl)butanoyl]pyrrolidine-3-carboxylic acid. A mixture of 277 mg (0.571 mmol) of the benzyl ester obtained in Example 162 Step A, benzyl 1-[(3R)-3-[(tert-butoxycarbonyl)amino]-4-(2-fluorophenyl)butanoyl]pyrrolidine-3-carboxylate, and 90 mg of 10% Pd/C in 80 mL of ethyl acetate was stirred under an atmosphere of hydrogen in a Parr shaker at 40 psi for 24 hr, filtered through Celite, and the Celite pad was washed with ethyl acetate. The filtrate was evaporated to yield 225 mg of the desired acid. MS: 295.1 (M=H). $^1$H NMR (500 MHz, CD$_3$OD) δ 7.27(m, 2H), 7.08(m, 2H), 4.41(m, 1H), 4.20(m, 1H), 3.61(m, 2H), 2.85 (m, 2H), 2.60(m, 2H), 2.22(m, 2H), 2.00(m, 2H), 1.90(m, 1H), 1.34((s, 9H).

Step C. Methyl (2S)-2-(4-{[({1-[(3R)-3-amino-4-(2-fluorophenyl)butanoyl]pyrrolidin-3-yl}carbonyl)amino]methyl}phenoxy)-3-methylbutanoate. To a solution of 35 mg (0.090 mmol) of 1-[(3R)-3-[(tert-butoxycarbonyl)amino]-4-(2-fluorophenyl)butanoyl]pyrrolidine-3-carboxylic acid obtained in Example 162 Step B in 3 mL of methylene chloride was added 26 mg (0.135 mmol) EDC and 12 mg (0.090 mmol) of 1-hydroxybenzotriazole hydrate (HOBT) followed by 30 mg (0.082 mmol) of the trifluoroacetate salt of ethyl (2S)-(4-aminomethylphenoxy)-3-methylbutanoate and 0.010 mL of diisopropyl ethyl amine. The reaction mixture was stirred for 16 hr and then applied to a prep TLC (silica) plate and eluted with 4% methanol 96% methylene chloride to recover the coupled amide. The amide was dissolved in 2 M HCl in methanol and stirred for two days. The reaction mixture was evaporated to yield 30 mg of the methyl ester. $^1$H NMR (500 MHz, CD$_3$OD) δ 7.34(m, 2H), 7.20(m, 4H), 6.80(m, 2H), 4.46(m, 3H), 4.28(m, 2H), 3.82(m, 1H), 3.71(s, 3H), 3.48(m, 4H), 3.08(m, 2H), 2.80(m, 1H), 2.58(m, 1H), 2.14(m, 2H), 1.96(m, 3H), 1.05(m, 6H).

Step D. (2S)-2-(4-{[({1-[(3R)-3-amino-4-(2-fluorophenyl)butanoyl]pyrrolidin-3-yl}carbonyl)amino]methyl}phenoxy)-3-methylbutanoic acid. To 15 mg (0.03 mmol) of methyl (2S)-2-(4-{[({1-[(3R)-3-amino-4-(2-fluorophenyl)butanoyl]pyrrolidin-3-yl}carbonyl)amino]methyl}phenoxy)-3-methylbutanoate obtained in Example 162 Step C in 1.5 mL of tetrahydrofuran/methanol (2:1), 0.1 mL of 1.0 M aqueous lithium hydroxide solution was added and the resultant mixture was stirred for 16 hr. Solvent was evaporated and a portion of the residue was dissolved in aqueous methanol and purified by reverse phase HPLC (column YMC ProC18, 100×20 mm, 5 um, solvent 90–10% water-acetonitrile) to give 1.5 mg of the desired product. $^1$H NMR (500 MHz, CD$_3$OD) δ 7.35(m, 2H), 7.20(m, 4H), 6.85(m, 2H), 4.41(m, 5H), 3.82(m, 1H), 3.48(m, 4H), 3.12 (m, 2H) 2.80(m, 1H), 2.60(m, 1H), 2.26(m, 2H), 1.96(m, 3H), 1.09(m, 6H).

What is claimed is:
1. A compound having Formula I:

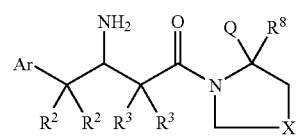

I including pharmaceutically acceptable salts and prodrugs thereof, wherein:
  X is selected from the group consisting of: $CR^{10}R^{11}$, S, SO, $SO_2$, and $CR^{10}R^9$, with the proviso that when X is $CR^{10}R^9$, Q and $R^8$ are both H;
  Ar is selected from the group consisting of:
    (1) phenyl,
    (2) naphthyl,
    (3) thienyl, and
    (4) benzothiophenyl;
  wherein Ar is optionally substituted with 1–5 groups $R^1$;
    $R^1$ is selected from the group consisting of:
    (1) halogen,
    (2) $C_{1-6}$alkyl, which is linear or branched and is optionally substituted with 1–5 halogens,
    (3) $OC_{1-6}$alkyl, which is linear or branched and is optionally substituted with 1–5 halogens, and
    (4) CN;
      Each $R^2$ is independently selected from the group consisting of H, OH, halogen and $C_{1-6}$alkyl, wherein $C_{1-6}$alkyl is linear or branched and is optionally substituted with 1–5 halogens, wherein the two groups $R^2$ can optionally be joined to form a $C_{3-6}$cycloalkyl, which is optionally substituted with 1–3 halogens;

Each $R^3$ is independently selected from the group consisting of H, halogen and $C_{1-6}$alkyl, wherein $C_{1-6}$alkyl is linear or branched and is optionally substituted with 1–5 halogens, wherein the two groups $R^3$ can optionally be joined to form a $C_{3-6}$cycloalkyl, which is optionally substituted with 1–3 halogens;

Q is selected from the group consisting of:
(1) H,
(2) C(=O)NR$^4$Z, and
(3) CN;

$R^4$ is selected from the group consisting of
(1) H, and
(2) $C_{1-6}$alkyl, which is linear or branched and is optionally substituted with 1–5 halogens;

Z is selected from the group consisting of:
(1) phenyl, which is optionally substituted with 1–5 substituents independently selected from halogen and $R^6$,
(2) $C_{1-6}$alkyl, which is linear or branched and is optionally substituted with 1–7 substituents independently selected from (a) 0–5 halogens, and (b) 0–2 substituents selected from the group consisting of
   (a) hydroxy,
   (b) $CO_2H$,
   (c) $CO_2C_{1-6}$alkyl,
   (d) phenyl,
   (e) naphthyl,
   (f) $C_{3-6}$cycloalkyl,
   (g) a 5- or 6-membered heterocycle which may be saturated or unsaturated comprising 1–4 heteroatoms independently selected from N, S and O; and
   (h) an 8–10 membered bicyclic ring system which may be saturated or unsaturated comprising (a) two fused heterocyclic rings, each heterocyclic ring having 1–4 heteroatoms selected from N, S and O, or (b) a benzene ring fused to a 5- or 6-membered heterocycle having 1–3 heteroatoms; wherein said $C_{3-6}$cycloalkyl, phenyl and naphthyl are optionally substituted with 1–5 substituents independently selected from halogen and $R^6$, and said 5 or 6-membered heterocycle and said 8–10 membered bicyclic ring system are each optionally substituted with 1–5 substituents independently selected from oxo, OH, halogen, and $R^6$; and
(3) $C_{3-6}$cycloalkyl, which is optionally substituted with 1–3 groups independently selected from halogen, hydroxy, $CO_2H$, $CO_2C_{1-6}$alkyl, $C_{1-6}$alkyl, and $OC_{1-6}$alkyl, said $CO_2C_{1-6}$alkyl, $C_{1-6}$alkyl, and $OC_{1-6}$alkyl being linear or branched and optionally substituted with 1–5 halogens;

$R^6$ is selected from the group consisting of:
(1) OH,
(2) CN,
(3) $C_{3-6}$cycloalkyl optionally substituted with 1–3 groups independently selected from hydroxy, halogen, $CO_2H$, $CO_2C_{1-6}$alkyl, $C_{1-6}$alkyl, and $OC_{1-6}$alkyl, wherein said $C_{1-6}$alkyl, $OC_{1-6}$alkyl and $CO_2C_{1-6}$alkyl are linear or branched and are optionally substituted with 1–6 substituents independently selected from 0–5 halogens and 0–1 substituents selected from $CO_2C_{1-6}$alkyl, $CO_2H$ and $OC_{1-6}$alkyl, said $CO_2C_{1-6}$alkyl and $OC_{1-6}$alkyl substituents being linear or branched and optionally substituted with 1–5 halogens,
(4) $C_{1-10}$alkyl, which is linear or branched and is optionally substituted with 1–7 substituents independently selected from 0–5 halogen atoms and 0–2 groups independently selected from
   (a) OH,
   (b) $CO_2H$,
   (c) $CO_2C_{1-6}$alkyl, which may be linear or branched and is optionally substituted with 1–5 halogens,
   (d) a 5- or 6-membered heterocycle which may be saturated or unsaturated comprising 1–4 heteroatoms independently selected from N, S and O, optionally substituted with 1–3 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
   (e) an 8–10 membered bicyclic ring system which may be saturated or unsaturated comprising (i) two fused heterocyclic rings, each heterocyclic ring having 1–4 heteroatoms independently selected from N, S and O, or (ii) a 5- or 6-membered heterocycle having 1–3 heteroatoms independently selected from N, S and O fused to a benzene ring, wherein said bicyclic ring system is optionally substituted with 1–5 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
   (f) $CONR^7R^7$,
   (g) $SO_2NR^7R^7$,
   (h) $NR^7C(O)R^7$,
   (i) $NR^7C(O)NR^7R^7$,
   (j) $NR^7CO_2R^5$,
   (k) $OC(O)R^7$,
   (l) $OC(O)NR^7R^7$,
   (m) $NR^7S(O)_2R^5$,
   (n) $NR^7R^7$,
   (o) phenyl, which is optionally substituted with 1–5 groups independently selected from halogen, OH, $C_{1-6}$alkyl, $OC_{1-6}$alkyl, $CO_2H$, and $CO_2C_{1-6}$alkyl, said $C_{1-6}$alkyl, $OC_{1-6}$alkyl, and $CO_2C_{1-6}$alkyl being linear or branched and optionally substituted with 1–6 substituents independently selected from 0–1 $C3-6$cycloalkyl and 0–5 halogens, and
   (p) $C_{3-6}$cycloalkyl, which is optionally substituted with 1–6 halogens;
(5) $OC_{1-10}$alkyl, which is linear or branched and is optionally substituted with 1–7 groups independently selected from 0–5 halogen atoms and 0–2 substituents selected from
   (a) OH,
   (b) $CO_2H$,
   (c) $CO_2C_{1-6}$alkyl, which may be linear or branched and is optionally substituted with 1–5 halogens,
   (d) a 5- or 6-membered heterocycle which may be saturated or unsaturated comprising 1–4 heteroatoms independently selected from N, S and O, optionally substituted with 1–3 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
   (e) an 8–10 membered bicyclic ring system which may be saturated or unsaturated comprising (i) two fused heterocyclic rings, each heterocyclic ring having 1–4 heteroatoms independently selected from N, S and O, or (ii) a 5- or 6-membered heterocycle having 1–3 heteroatoms independently selected from N, S and O fused to a benzene ring, wherein said bicyclic ring system is optionally substituted with 1–5 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;

(f) $CONR^7R^7$,
(g) $SO_2NR^7R^7$,
(h) $NR^7C(O)R^7$,
(i) $NR^7C(O)NR^7R^7$,
(j) $NR^7CO_2R^5$,
(k) $OC(O)R^7$,
(l) $OC(O)NR^7R^7$,
(m) $NR^7S(O)_2R^5$,
(n) $NR^7R^7$,
(o) phenyl, which is optionally substituted with 1–5 groups independently selected from halogen, OH, $C_{1-6}$alkyl, $OC_{1-6}$alkyl, $CO_2H$, and $CO_2C_{1-6}$alkyl, said $C_{1-6}$alkyl, $OC_{1-6}$alkyl, and $CO_2C_{1-6}$alkyl being linear or branched and optionally substituted with 1–6 substituents independently selected from 0–1 $C3$-$6$cycloalkyl and 0–5 halogens, and
(p) $C_{3-6}$cycloalkyl, which is optionally substituted with 1–6 halogens;
(6) $CO_2H$;
(7) $CO_2C_{1-6}$alkyl, which may be linear or branched and is optionally substituted with 1–5 halogens;
(8) a 5- or 6-membered heterocycle which may be saturated or unsaturated comprising 1–4 heteroatoms independently selected from N, S and O, said heterocycle being optionally substituted with 1–3 substituents independently selected from oxo, OH, halogen, $C_{1-6}$alkyl, and $OC_{1-6}$alkyl, said $C_{1-6}$alkyl and $OC_{1-6}$alkyl being linear or branched and optionally subtitued with 1–5 halogens;
(9) an 8–10 membered bicyclic ring system which may be saturated or unsaturated comprising (a) two fused heterocyclic rings, each heterocyclic ring having 1–4 heteroatoms independently selected from N, S and O, or (b) a 5- or 6-membered heterocycle having 1–3 heteroatoms independently selected from N, S and O fused to a benzene ring, said bicyclic ring system being optionally substituted with 1–5 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
(10) $CONR^7R^7$;
(11) $SO_{02}NR^7R^7$;
(12) $NR^7C(O)R^7$;
(13) $NR^7C(O)NR^7R^7$;
(14) $NR^7CO_2R^5$;
(15) $OC(O)R^7$;
(16) $OC(O)NR^7R^7$;
(17) $NR^7S(O)_2R^5$;
(18) $NR^7R^7$; and
(19) phenyl, which is optionally substituted with 1–5 groups independently selected from halogen, OH, $C_{1-6}$alkyl, $OC_{1-6}$alkyl, $CO_2H$, and $CO_2C_{1-6}$alkyl, said $C_{1-6}$alkyl, $OC_{1-6}$alkyl, and $CO_2C_{1-6}$alkyl being linear or branched and optionally substituted with 1–5 halogens;

$R^5$ is selected from the group consisting of phenyl, $C_{3-6}$cycloalkyl and $C_{1-6}$alkyl, wherein $C_{1-6}$alkyl is linear or branched and is optionally substituted with 1–6 substituents independently selected from 0–5 halogens and 0–1 phenyl, wherein said optional phenyl substituent and said $R_5$ when $R^5$ is phenyl or $C_{3-6}$cycloalkyl are optionally substituted with 1–5 substituents independently selected from halogen, OH, $C_{1-6}$alkyl, and $OC_{1-5}$alkyl, said $C_{1-5}$alkyl and $OC_{1-5}$alkyl being linear or branched and optionally substituted with 1–5 halogens;

$R^7$ is selected from
(1) H, and
(2) $R^5$;

$R^8$ is selected from
(1) H, and
(2) $C_{1-6}$alkyl, which is linear or branched and is optionally substituted with 1–5 halogens;

$R^9$ is $C(=O)NR^4Z$; and $R^{10}$ and $R^{11}$ are each selected from the group consisting of H, F and $C_{1-6}$ alkyl, which is linear or branched and is optionally substituted with 1–5 halogens.

2. A compound having formula I as recited in claim 1, wherein $R_2$ and $R_3$ are H.

3. A compound having formula I as recited in claim 1, wherein Ar is phenyl, which is optionally substituted as in claim 1.

4. A compound having Formula I as recited in claim 1, wherein $R^4$ is H.

5. A compound having Formula I as recited in claim 1, wherein Q is $C(=O)NHZ$, Z is selected from $CH_2$phenyl, cyclohexyl and cyclopentyl, and $R^9$ is $C(=O)NHCH_2$phenyl, where phenyl, cyclohexyl and cyclopentyl are optionally substituted as in claim 1.

6. A compound having Formula I as recited in claim 1, wherein $R^8$ is H.

7. A compound having Formula I as recited in claim 1, wherein said 8–10 membered bicyclic ring system is selected from the group consisting of indole, indoline, benzofuran, benzothiophene, benzoxazole, benzisoxazole, benzothiazole, benzisothiazole, benzimidazole, benzimidazoline, quinoline, quinazoline, dihydroquinazoline, dihydroquinoline, isoquinoline, tetrahydroisoquinoline, and dihydroisoquinoline.

8. A compound having Formula I as recited in claim 1, wherein said 5- or 6-membered heterocycle is selected from the group consisting of furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine and tetrazolidine.

9. A compound having Formula Ia:

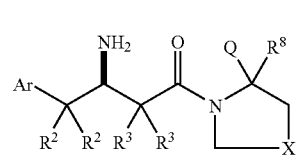

including pharmaceutically acceptable salts and prodrugs thereof, wherein:

X is selected from the group consisting of: $CR^{10}R^{11}$, S, SO, $SO_2$, and $CR^{10}R^9$, with the proviso that when X is $CR^{10}R^9$, Q and $R^8$ are both H;

Ar is selected from the group consisting of:
(1) phenyl,
(2) naphthyl,
(3) thienyl, and
(4) benzothiophenyl;
wherein Ar is optionally substituted with 1–5 groups $R^1$;
$R^1$ is selected from the group consisting of:
(1) halogen,
(2) $C_{1-6}$alkyl, which is linear or branched and is optionally substituted with 1–5 halogens,
(3) $OC_{1-6}$alkyl, which is linear or branched and is optionally substituted with 1–5 halogens, and
(4) CN;
Each $R^2$ is independently selected from the group consisting of H, OH, halogen and $C_{1-6}$alkyl, wherein $C_{1-6}$alkyl is linear or branched and is optionally substituted with 1–5 halogens, wherein the two groups $R^2$ can optionally be joined to form a $C_{3-6}$cycloalkyl, which is optionally substituted with 1–3 halogens;
Each $R^3$ is independently selected from the group consisting of H, halogen and $C_{1-6}$alkyl, wherein $C_{1-6}$alkyl is linear or branched and is optionally substituted with 1–5 halogens, wherein the two groups $R^3$ can optionally be joined to form a $C_{3-6}$cycloalkyl, which is optionally substituted with 1–3 halogens;
Q is selected from the group consisting of:
(1) H,
(2) $C(=O)NR^4Z$, and
(3) CN;
$R^4$ is selected from the group consisting of
(1) H, and
(2) $C_{1-6}$alkyl, which is linear or branched and is optionally substituted with 1–5 halogens;
Z is selected from the group consisting of:
(1) phenyl, which is optionally substituted with 1–5 substituents independently selected from halogen and $R^6$,
(2) $C_{1-6}$alkyl, which is linear or branched and is optionally substituted with 1–7 substituents independently selected from (a) 0–5 halogens, and (b) 0–2 substituents selected from the group consisting of
(a) hydroxy,
(b) $CO_2H$,
(c) $CO_2C_{1-6}$alkyl,
(d) phenyl,
(e) naphthyl,
(f) $C_{3-6}$ cycloalkyl,
(g) a 5- or 6-membered heterocycle which may be saturated or unsaturated comprising 1–4 heteroatoms independently selected from N, S and O; and
(h) an 8–10 membered bicyclic ring system which may be saturated or unsaturated comprising (a) two fused heterocyclic rings, each heterocyclic ring having 1–4 heteroatoms selected from N, S and O, or (b) a benzene ring fused to a 5- or 6-membered heterocycle having 1–3 heteroatoms; wherein said $C_{3-6}$cycloalkyl, phenyl and naphthyl are optionally substituted with 1–5 substituents independently selected from halogen and $R^6$, and said 5 or 6-membered heterocycle and said 8–10 membered bicyclic ring system are each optionally substituted with 1–5 substituents independently selected from oxo, OH, halogen, and $R^6$; and (3) $C_{3-6}$cycloalkyl, which is optionally substituted with 1–3 groups independently selected from halogen, hydroxy, $CO_2H$, $CO_2C_{1-6}$alkyl, $C_{1-6}$alkyl, and $OC_{1-6}$alkyl, said $CO_2C_{1-6}$alkyl, $C_{1-6}$alkyl, and $OC_{1-6}$alkyl being linear or branched and optionally substituted with 1–5 halogens;
$R^6$ is selected from the group consisting of:
(1) OH,
(2) CN,
(3) $C_{3-6}$cycloalkyl optionally substituted with 1–3 groups independently selected from hydroxy, halogen, $CO_2H$, $CO_2C_{1-6}$alkyl, $C_{1-6}$ alkyl, and $OC_{1-6}$alkyl, wherein said $C_{1-6}$alkyl, $OC_{1-6}$alkyl and $CO_2C_{1-6}$alkyl are linear or branched and are optionally substituted with 1–6 substituents independently selected from 0–5 halogens and 0–1 substituents selected from $CO_2C_{1-6}$alkyl, $CO_2H$ and $OC_{1-6}$alkyl, said $CO_2C_{1-6}$alkyl and $OC_{1-6}$alkyl substituents being linear or branched and optionally substituted with 1–5 halogens,
(4) $C_{1-10}$alkyl, which is linear or branched and is optionally substituted with 1–7 substituents independently selected from 0–5 halogen atoms and 0–2 groups independently selected from
(a) OH,
(b) $CO_2H$,
(c) $CO_2C_{1-6}$alkyl, which may be linear or branched and is optionally substituted with 1–5 halogens,
(d) a 5- or 6-membered heterocycle which may be saturated or unsaturated comprising 1–4 heteroatoms independently selected from N, S and O, optionally substituted with 1–3 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
(e) an 8–10 membered bicyclic ring system which may be saturated or unsaturated comprising (i) two fused heterocyclic rings, each heterocyclic ring having 1–4 heteroatoms independently selected from N, S and O, or (ii) a 5- or 6-membered heterocycle having 1–3 heteroatoms independently selected from N, S and O fused to a benzene ring, wherein said bicyclic ring system is optionally substituted with 1–5 substituents independently selected from oxo, OH, halogen, $C_{1-6}$alkyl, and $OC_{1-6}$alkyl, said $C_{1-6}$alkyl and $OC_{1-6}$alkyl being halogens;
(f) $CONR^7R^7$,
(g) $SO_2NR^7R^7$,
(h) $NR^7C(O)R^7$,
(i) $NR^7C(O)NR^7R^7$,
(j) $NR^7CO_2R^5$,
(k) $OC(O)R^7$,
(l) $OC(O)NR^7R^7$,
(m) $NR^7S(O)_2R^5$,
(n) $NR^7R^7$,
(o) phenyl, which is optionally substituted with 1–5 groups independently selected from halogen, OH, $C_{1-6}$alkyl, $OC_{1-6}$alkyl, $CO_2H$, and $CO_2C_{1-6}$alkyl, said $C_{1-6}$alkyl, $OC_{1-6}$alkyl, and $CO_2C_{1-6}$alkyl being linear or branched and optionally substituted with 1–6 substituents independently selected from 0–1 $C_{3-6}$cycloalkyl and 0–5 halogens, and
(p) $C_{3-6}$cycloalkyl, which is optionally substituted with 1–6 halogens;
(5) $OC_{1-10}$alkyl, which is linear or branched and is optionally substituted with 1–7 groups independently selected from 0–5 halogen atoms and 0–2 substituents selected from (a) OH,
(b) $CO_2H$,
(c) $CO_2C_{1-6}$alkyl, which may be linear or branched and is optionally substituted with 1–5 halogens,
(d) a 5- or 6-membered heterocycle which may be saturated or unsaturated comprising 1–4 heteroatoms independently selected from N, S and O, optionally substituted with 1–3 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
(e) an 8–10 membered bicyclic ring system which may be saturated or unsaturated comprising (i) two fused heterocyclic rings, each heterocyclic ring having 1–4 heteroatoms independently selected from N, S and O, or (ii) a 5- or 6-membered heterocycle having 1–3 heteroatoms independently selected from N, S and O fused to a benzene ring, wherein said bicyclic ring system is optionally substituted with 1–5 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
(f) $CONR^7R^7$,
(g) $SO_2NR^7R^7$,
(h) $NR^7C(O)R^7$,
(i) $NR^7C(O)NR^7R^7$,
(j) $NR^7CO_2R^5$,
(k) $OC(O)R^7$,
(l) $OC(O)NR^7R^7$,
(m) $NR^7S(O)_2R^5$,
(n) $NR^7R^7$,
(o) phenyl, which is optionally substituted with 1–5 groups independently selected from halogen, OH, $C_{1-6}$alkyl, $OC_{1-6}$alkyl, $CO_2H$, and $CO_2C_{1-6}$alkyl, said $C_{1-6}$alkyl, $OC_{1-6}$alkyl, and $CO_2C_{1-6}$alkyl being linear or branched and optionally substituted with 1–6 substituents independently selected from 0–1 $C_{3-6}$cycloalkyl and 0–5 halogens, and
(p) $C_{3-6}$cycloalkyl, which is optionally substituted with 1–6 halogens;
(6) $CO_2H$;
(7) $CO_2C_{1-6}$alkyl, which may be linear or branched and is optionally substituted with 1–5 halogens;
(8) a 5- or 6-membered heterocycle which may be saturated or unsaturated comprising 1–4 heteroatoms independently selected from N, S and O, said heterocycle being optionally substituted with 1–3 substituents independently selected from oxo, OH, halogen, $C_{1-6}$alkyl, and $OC_{1-6}$alkyl, said $C_{l-6}$alkyl and $OC_{1-6}$alkyl being linear or branched and optionally substituted with 1–5 halogens;
(9) an 8–10 membered bicyclic ring system which may be saturated or unsaturated comprising (a) two fused heterocyclic rings, each heterocyclic ring having 1–4 heteroatoms independently selected from N, S and O, or (b) a 5- or 6-membered heterocycle having 1–3 heteroatoms independently selected from N, S and O fused to a benzene ring, said bicyclic ring system being optionally substituted with 1–5 substituents independently selected from oxo, OH, halogen, $C_{1-6}$alkyl, and $OC_{1-6}$alkyl, said $C_{1-6}$alkyl and $OC_{1-6}$alkyl being linear or branched and optionally substituted with 1–5 halogens;
(10) $CONR^7R^7$;
(11) $SO_2NR^7R^7$;
(12) $NR^7C(O)R^7$;
(13) $NR^7C(O)NR^7R^7$;
(14) $NR^7CO_2R^5$;
(15) $OC(O)R^7$;
(16) $OC(O)NR^7R^7$;
(17) $NR^7S(O)_2R^5$;
(18) $NR^7R^7$; and
(19) phenyl, which is optionally substituted with 1–5 groups independently selected from halogen, OH, $C_{1-6}$alkyl, $OC_{1-6}$alkyl, $CO_2H$, and $CO_2C_{1-6}$alkyl, said $C_{1-6}$alkyl, $OC_{1-6}$alkyl, and $CO_2C_{1-6}$alkyl being linear or branched and optionally substituted with 1–5 halogens;

$R^5$ is selected from the group consisting of phenyl, $C_{3-6}$cycloalkyl and $C_{1-6}$alkyl, wherein $C_{1-6}$alkyl is linear or branched and is optionally substituted with 1–6 substituents independently selected from 0–5 halogens and 0–1 phenyl, wherein said optional phenyl substituent and said $R^5$ when $R^5$ is phenyl or $C_{3-6}$cycloalkyl are optionally substituted with 1–5 substituents independently selected from halogen, OH, $C_{1-5}$alkyl, and $OC_{1-5}$alkyl, said $C_{1-5}$alkyl and $OC_{1-5}$alkyl being linear or branched and optionally substituted with 1–5 halogens;

$R^7$ is selected from
(1) H, and
(2) $R^5$;

$R^8$ is selected from
(1) H, and
(2) $C_{1-6}$alkyl, which is linear or branched and is optionally substituted with 1–5 halogens;

$R^9$ is $C(=O)NR^4Z$; and $R^{10}$ and $R^{11}$ are each selected from the group consisting of H, F and $C_{1-6}$alkyl, which is linear or branched and is optionally substituted with 1–5 halogens.

10. A compound having formula Ia as recited in claim 9, wherein $R_2$ and $R_3$ are H.

11. A compound having formula Ia as recited in claim 9, wherein Ar is phenyl, which is optionally substituted as in claim 1.

12. A compound having Formula Ia as recited in claim 9, wherein $R^4$ is H.

13. A compound having Formula Ia as recited in claim 9, wherein Q is $C(=O)NHZ$, Z is selected from $CH_2$phenyl, cyclohexyl and cyclopentyl, and $R^9$ is $C(=O)NHCH_2$phenyl, where phenyl, cyclohexyl and cyclopentyl are optionally substituted as in claim 1.

14. A compound having Formula Ia as recited in claim 9, wherein $R^8$ is H.

15. A compound having Formula Ia as recited in claim 9, wherein said 8–10 membered bicyclic ring system is selected from the group consisting of indole, indoline, benzofuran, benzothiophene, benzoxazole, benzisoxazole, benzothiazole, benzisothiazole, benzimidazole, benzimidazoline, quinoline, quinazoline, dihydroquinazoline, dihydroquinoline, isoquinoline, tetrahydroisoquinoline, and dihydroisoquinoline.

16. A compound having Formula Ia as recited in claim 9, wherein said 5- or 6-membered heterocycle is selected from the group consisting of furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, tetrazolidine, and triazolidine.

17. A compound having Formula Ib:

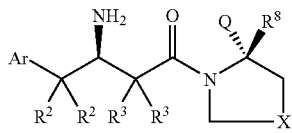

including pharmaceutically acceptable salts and prodrugs thereof, wherein Ar, $R^1$, $R^2$, $R^3$, $R^4$, $R^5$, $R^6$, $R^7$, $R^8$, $R^9$, $R^{10}$, $R^{11}$, X, Q and Z are as defined in any of claims 1–16.

18. A pharmaceutical composition comprising a compound of claim 1 and a pharmaceutically acceptable carrier.

19. A method for treating, controlling, or preventing non-insulin dependent (Type 2) diabetes mellitus in a mammalian patient in need of such treatment which comprises administering to said patient a therapeutically effective amount of a compound of claim 1.

* * * * *